(12) United States Patent
Mitchell et al.

(10) Patent No.: US 7,928,084 B2
(45) Date of Patent: Apr. 19, 2011

(54) REGULATION OF INTEGRIN SURFACE EXPRESSION

(75) Inventors: W. Beau Mitchell, Long Island, NY (US); Mahmoud Yazdani Abyaneh, Brooklyn, NY (US); Amanda Chen, Brooklyn, NY (US)

(73) Assignee: New York Blood Center, Inc., New York, NY (US)

( * ) Notice: Subject to any disclaimer, the term of this patent is extended or adjusted under 35 U.S.C. 154(b) by 0 days.

(21) Appl. No.: 12/543,836

(22) Filed: Aug. 19, 2009

(65) Prior Publication Data

US 2010/0048677 A1 Feb. 25, 2010

Related U.S. Application Data

(60) Provisional application No. 61/090,488, filed on Aug. 20, 2008.

(51) Int. Cl.
*A61K 31/70* (2006.01)
*C07H 21/04* (2006.01)
(52) U.S. Cl. .......................................... 514/44; 536/24.5
(58) Field of Classification Search .......................... None
See application file for complete search history.

(56) References Cited

OTHER PUBLICATIONS

Corazzari M et al. "Targeting homeostatic mechanisms of endoplasmic reticulum stress to increase susceptibility of cancer cells to fenretinide-induced apoptosis: the role of stress proteins ERdj5 and ERp57." Br. J. Cancer 96:1062-1071, 2007.
Cunnea P et al. "Increased expression of specific thioredoxin family proteins: a pilot immunohistochemical study on human hepatocellular carcinoma." Int. J. Immunopath. Pharmacol. 20:17-24, 2007.
Wilcox DA et al. "Megakaryocyte-targeted synthesis of the integrin beta3-subunit results in the phenotypic correction of Glanzmann thrombocytopenia." Blood 95:3645-3652, 2000.
Chen A et al. "Proteomic analysis of the alphaIIbbeta3 interatome reveals novel chaperone and trafficking proteins, including an HSP40 chaperone, DNAJC10, that regulations alphaIIbbeta3 surface expression." Blood 112:987-988, 2008.
Chen P et al. Differential display identifies genes in Chinese hamster ovary cells sensitive to elevated ammonium. Appl. Biochem. Biotechnol. 141:349-359, 2007.
Gu SH et al. "and identification of a novel cDNA which encodes a putative protein with a DnaJ domain and a thioredoxin active motif, human macrothioredoxin." Biochem. Genet. 41:245-253, 2003.
Ushioda R et al. "ERdj5 is required as a disulfide reductase for degradation of misfolded proteins in the ER." Science 321:569-572, 2008.
Cunnea PM et al. "ERdj5, an endoplasmic reticulum (ER)-resident protein containing DnaJ and thoredoxin domains, is expressed in secretory cells or following ER stress." J. Biol. Chem. 278:1059-1066, 2003.
Dong M et al. "ERdj4 and ERdj5 are required for endoplasmic reticulum-associated protein degradation of misfolded surfactant protein C." Mol. Biol. of the Cell 19:2620-2630, 2008.
Golden A et al. "Role of platelet membrane glycoprotein IIb-IIIa in agonist-induced tyrosine phosphorylation of platelet proteins." J. Cell Biol. 111:3117-3127, 1990.
Braakman I et al. "Biochemistry. Cargo load reduction." Science 321:499-500, 2008.
Kolodzief Ma et al. "Study of the endoproteolytic cleavage of platelet glycopretein IIb using oligonucleotide-mediated mutagenesis." J. Biol. Chem. 266:23499-23504, 1991.
Plancon S et al. "Green Fluorescent protein (GFP) tagged to the cytoplasmic tail of alphaIIb or beta3 allows the expression of a fully functional integrin alphaIIbbeta3: effect of beta3-GFP on alphaIIb-beta3 ligand binding." Biochem. J. 357:529-536, 2001.

*Primary Examiner* — Tracy Vivlemore
(74) *Attorney, Agent, or Firm* — K&L Gates LLP; Louis C. Cullman; Michelle Glasky Bergman

(57) ABSTRACT

Disclosed are methods and compositions for preventing and treating conditions associated with platelet aggregation, comprising administering a therapeutically effective amount of a composition that modifies the interaction of DNAJC10 with αIIbβ3 in a megakaryocyte, thereby altering the expression of αIIbβ3 on the surface of the megakaryocyte.

7 Claims, 5 Drawing Sheets

```
                        SEQUENCE LISTING

<160> NUMBER OF SEQ ID NOS: 6

<210> SEQ ID NO 1
<211> LENGTH: 793
<212> TYPE: PRT
<213> ORGANISM: Homo sapiens

<400> SEQUENCE: 1

Met Gly Val Trp Leu Asn Lys Asp Asp Tyr Ile Arg Asp Leu Lys Arg
1               5                   10                  15

Ile Ile Leu Cys Phe Leu Ile Val Tyr Met Ala Ile Leu Val Gly Thr
                20                  25                  30

Asp Gln Asp Phe Tyr Ser Leu Leu Gly Val Ser Lys Thr Ala Ser Ser
            35                  40                  45

Arg Glu Ile Arg Gln Ala Phe Lys Lys Leu Ala Leu Lys Leu His Pro
    50                  55                  60

Asp Lys Asn Pro Asn Asn Pro Asn Ala His Gly Asp Phe Leu Lys Ile
65                  70                  75                  80

Asn Arg Ala Tyr Glu Val Leu Lys Asp Glu Asp Leu Arg Lys Lys Tyr
                85                  90                  95

Asp Lys Tyr Gly Glu Lys Gly Leu Glu Asp Asn Gln Gly Gly Gln Tyr
                100                 105                 110

Glu Ser Trp Asn Tyr Tyr Arg Tyr Asp Phe Gly Ile Tyr Asp Asp Asp
            115                 120                 125

Pro Glu Ile Ile Thr Leu Glu Arg Arg Glu Phe Asp Ala Ala Val Asn
        130                 135                 140

Ser Gly Glu Leu Trp Phe Val Asn Phe Tyr Ser Pro Gly Cys Ser His
145                 150                 155                 160

Cys His Asp Leu Ala Pro Thr Trp Arg Asp Phe Ala Lys Glu Val Asp
                165                 170                 175

Gly Leu Leu Arg Ile Gly Ala Val Asn Cys Gly Asp Asp Arg Met Leu
            180                 185                 190

Cys Arg Met Lys Gly Val Asn Ser Tyr Pro Ser Leu Phe Ile Phe Arg
        195                 200                 205

Ser Gly Met Ala Pro Val Lys Tyr His Gly Asp Arg Ser Lys Glu Ser
    210                 215                 220
```

```
Leu Val Ser Phe Ala Met Gln His Val Arg Ser Thr Val Thr Glu Leu
225                 230                 235                 240

Trp Thr Gly Asn Phe Val Asn Ser Ile Gln Thr Ala Phe Ala Ala Gly
                245                 250                 255

Ile Gly Trp Leu Ile Thr Phe Cys Ser Lys Gly Gly Asp Cys Leu Thr
            260                 265                 270

Ser Gln Thr Arg Leu Arg Leu Ser Gly Met Leu Asp Gly Leu Val Asn
        275                 280                 285

Val Gly Trp Met Asp Cys Ala Thr Gln Asp Asn Leu Cys Lys Ser Leu
    290                 295                 300

Asp Ile Thr Thr Ser Thr Thr Ala Tyr Phe Pro Gly Ala Thr Leu
305                 310                 315                 320

Asn Asn Lys Glu Lys Asn Ser Ile Leu Phe Leu Asn Ser Leu Asp Ala
                325                 330                 335

Lys Glu Ile Tyr Leu Glu Val Ile His Asn Leu Pro Asp Phe Glu Leu
            340                 345                 350

Leu Ser Ala Asn Thr Leu Glu Asp Arg Leu Ala His His Arg Trp Leu
        355                 360                 365

Leu Phe Phe His Phe Gly Lys Asn Glu Asn Ser Asn Asp Pro Glu Leu
    370                 375                 380

Lys Lys Leu Lys Thr Leu Leu Lys Asn Asp His Ile Gln Val Gly Arg
385                 390                 395                 400

Phe Asp Cys Ser Ser Ala Pro Asp Ile Cys Ser Asn Leu Tyr Val Phe
                405                 410                 415

Gln Pro Ser Leu Ala Val Phe Lys Gly Gln Gly Thr Lys Glu Tyr Glu
            420                 425                 430

Ile His His Gly Lys Lys Ile Leu Tyr Asp Ile Leu Ala Phe Ala Lys
        435                 440                 445

Glu Ser Val Asn Ser His Val Thr Thr Leu Gly Pro Gln Asn Phe Pro
    450                 455                 460

Ala Asn Asp Lys Glu Pro Trp Leu Val Asp Phe Phe Ala Pro Trp Cys
465                 470                 475                 480

Pro Pro Cys Arg Ala Leu Leu Pro Glu Leu Arg Arg Ala Ser Asn Leu
                485                 490                 495

Leu Tyr Gly Gln Leu Lys Phe Gly Thr Leu Asp Cys Thr Val His Glu
            500                 505                 510

Gly Leu Cys Asn Met Tyr Asn Ile Gln Ala Tyr Pro Thr Thr Val Val
        515                 520                 525

Phe Asn Gln Ser Asn Ile His Glu Tyr Glu Gly His His Ser Ala Glu
    530                 535                 540

Gln Ile Leu Glu Phe Ile Glu Asp Leu Met Asn Pro Ser Val Val Ser
545                 550                 555                 560

Leu Thr Pro Thr Thr Phe Asn Glu Leu Val Thr Gln Arg Lys His Asn
                565                 570                 575

Glu Val Trp Met Val Asp Phe Tyr Ser Pro Trp Cys His Pro Cys Gln
            580                 585                 590

Val Leu Met Pro Glu Trp Lys Arg Met Ala Arg Thr Leu Thr Gly Leu
        595                 600                 605

Ile Asn Val Gly Ser Ile Asp Cys Gln Gln Tyr His Ser Phe Cys Ala
    610                 615                 620

Gln Glu Asn Val Gln Arg Tyr Pro Glu Ile Arg Phe Phe Pro Pro Lys
625                 630                 635                 640

Ser Asn Lys Ala Tyr His Tyr His Ser Tyr Asn Gly Trp Asn Arg Asp
```

```
                        645                 650                 655
Ala Tyr Ser Leu Arg Ile Trp Gly Leu Gly Phe Leu Pro Gln Val Ser
                660                 665                 670

Thr Asp Leu Thr Pro Gln Thr Phe Ser Glu Lys Val Leu Gln Gly Lys
            675                 680                 685

Asn His Trp Val Ile Asp Phe Tyr Ala Pro Trp Cys Gly Pro Cys Gln
        690                 695                 700

Asn Phe Ala Pro Glu Phe Glu Leu Leu Ala Arg Met Ile Lys Gly Lys
705                 710                 715                 720

Val Lys Ala Gly Lys Val Asp Cys Gln Ala Tyr Ala Gln Thr Cys Gln
                725                 730                 735

Lys Ala Gly Ile Arg Ala Tyr Pro Thr Val Lys Phe Tyr Phe Tyr Glu
            740                 745                 750

Arg Ala Lys Arg Asn Phe Gln Glu Glu Gln Ile Asn Thr Arg Asp Ala
        755                 760                 765

Lys Ala Ile Ala Ala Leu Ile Ser Glu Lys Leu Glu Thr Leu Arg Asn
    770                 775                 780

Gln Gly Lys Arg Asn Lys Asp Glu Leu
785                 790

<210> SEQ ID NO 2
<211> LENGTH: 4193
<212> TYPE: DNA
<213> ORGANISM: Homo sapiens

<400> SEQUENCE: 2
agaccggcgc gtgaggaacc taccggtacc ggccgcgcgc tggtagtcgc cggtgtggct     60
gcacctcacc aatcccgtgc gccgcggctg ggccgtcgga gagtgcgtgt gcttctctcc    120
tgcacgcggt gcttgggctc ggccaggcgg ggtccgccgc cagggtttga ggatggggga    180
gtagctacag gaagcgaccc cgcgatggca aggtatattt ttgtggaatg aaaaggaagt    240
attgaaaatg agctgaagac cattcacaga ttaatatttt tggggacaga tttgtgatgc    300
ttgattcacc cttgaagtaa tgtagacaga agttctcaaa tttgcatatt acatcaactg    360
gaaccagcag tgaatcttaa tgttcactta aatcagaact tgcataagaa agagaatggg    420
agtctggtta aataaagatg actatatcag agacttgaaa aggatcattc tctgttttct    480
gatagtgtat atggccattt tagtgggcac agatcaggat ttttacagtt tacttggagt    540
gtccaaaact gcaagcagta gagaaataag acaagctttc aagaaattgg cattgaagtt    600
acatcctgat aaaaacccga taacccaaa tgcacatggc gatttttaa aaataaatag      660 agcatatgaa gtactcaaag atgaagatct acggaaaaag tatgacaaat atggagaaaa    720
gggacttgag gataatcaag gtggccagta tgaaagctgg aactattatc gttatgattt    780
tggtatttat gatgatgatc ctgaaatcat aacattggaa agaagagaat tgatgctgc     840 tgttaattct ggagaactgt ggtttgtaaa ttttactcc ccaggctgtt cacactgcca     900
tgatttagct cccacatgga gactttgc taaagaagtg gatgggttac ttcgaattgg      960
agctgttaac tgtggtgatg atagaatgct ttgccgaatg aaaggagtca acagctatcc   1020
cagcctcttc atttttcggt ctggaatggc cccagtgaaa tatcatggag acagatcaaa   1080
ggagagttta gtgagttttg caatgcagca tgttagaagt acagtgacag aactttggac   1140
aggaaatttt gtcaactcca tacaaactgc ctttgctgct ggtattggct ggctgatcac   1200 ttttgttca aaaggaggag attgtttgac ttcacagaca cgactcaggc ttagtggcat   1260
gttggatggt cttgttaatg taggatggat ggactgtgcc acccaggata acctttgtaa   1320
```

```
aagcttagat attacaacaa gtactactgc ttattttcct cctggagcca ctttaaataa    1380
caaagagaaa aacagtattt tgtttctcaa ctcattggat gctaaagaaa tatatttgga    1440
agtaatacat aatcttccag attttgaact actttcggca aacacactag aggatcgttt    1500
ggctcatcat cggtggctgt tattttttca ttttggaaaa aatgaaaatt caaatgatcc    1560
tgagctgaaa aaactaaaaa ctctacttaa aaatgatcat attcaagttg gcaggtttga    1620
ctgttcctct gcaccagaca tctgtagtaa tctgtatgtt tttcagccgt ctctagcagt    1680
atttaaagga caaggaacca agaatatga aattcatcat ggaaagaaga ttctatatga    1740
tatacttgcc tttgccaaag aaagtgtgaa ttctcatgtt accacgcttg gacctcaaaa    1800
ttttcctgcc aatgacaaag aaccatggct tgttgatttc tttgccccct ggtgtccacc    1860
atgtcgagct ttactaccag agttacgaag agcatcaaat cttctttatg gtcagcttaa    1920
gtttggtaca ctagattgta cagttcatga gggactctgt aacatgtata acattcaggc    1980
ttatccaacg acagtggtat tcaaccagtc aacattcat gagtatgaag acatcactc      2040 tgctgaacaa atcttggagt tcatagagga tcttatgaat ccttcagtgg tctcccttac    2100
acccaccacc ttcaacgaac tagttacaca agaaaacac aacgaagtct ggatggttga     2160
tttctattct ccgtggtgtc atccttgcca agtcttaatg ccagaatgga aaagaatggc    2220
ccggacatta actggactga tcaacgtggg cagtatagat tgccaacagt atcattcttt    2280
ttgtgcccag gaaaacgttc aaagatacc tgagataaga ttttttcccc caaaatcaaa     2340
taaagcttat cattatcaca gttacaatgg ttggaatagg gatgcttatt ccctgagaat    2400
ctggggtcta ggattttac ctcaagtatc cacagatcta acacctcaga cttcagtga      2460 aaaagttcta caaggaaaa atcattgggt gattgatttc tatgctccctt ggtgtggacc    2520 ttgccagaat tttgctccag aatttgagct cttggctagg atgattaaag gaaaagtgaa    2580
agctggaaaa gtagactgtc aggcttatgc tcagacatgc cagaaagctg ggatcagggc    2640
ctatccaact gttaaatttt atttctacga aagagcaaag agaaattttc aagaagagca    2700
gataaatacc agagatgcaa aagcaatcgc tgccttaata agtgaaaaat tggaaactct    2760
ccgaaatcaa ggcaagagga ataaggatga actttgataa tgttgaagat gaagaaaaag    2820
tttaaaagaa attctgacag atgacatcag aagacaccta tttagaatgt tacatttatg    2880
atgggaatga atgaacatta tcttagactt gcagttgtac tgccagaatt atctacagca    2940
ctggtgtaaa agaagggtct gcaaactttt tctgtaaagg gccggtttat aaatatttta    3000
gactttgcag gctataatat atggttcaca catgagaaca agaatagagt catcatgtat    3060
tctttgttat ttgcttttaa caaccttta aaaatattaa aacgattctt agctcagagc     3120
catacaaaag taggctggat tcagtccatg gaccatagat tgctgtcccc ctcgacggac    3180
ttataatgtt tcaggtggct ggcttgaaca tgagtctgct gtgctatcta cataaatgtc    3240
taagttgtat aaagtccact ttcccttcac gttttttggc tgacctgaaa agaggtaact    3300 tagttttttgg tcacttgttc tcctaaaaat gctatcccta accatatatt tatatttcgt    3360
tttaaaaaca cccatgatgt ggcacagtaa acaaaccctg ttatgctgta ttattatgag    3420
gagattcttc attgttttct ttccttctca aaggttgaaa aatgctttt aattttttcac    3480 agccgagaaa cagtgcagca gtatatgtgc acacagtaag tacacaaatt tgagcaacag    3540
taagtgcaca aattctgtag tttgccgtat catccaggaa aacctgaggg aaaaaaatta    3600
tagcaattaa ctgggcattg tagagtatcc taaaatgtt atcaagtatt tagagttcta     3660
tattttaaag atatatgtgt tcatgtattt tctgaaattg ctttcataga aattttccca    3720
```

-continued

```
ctgatagttg attttgagg catctaatat ttacatattt gccttctgaa ctttgttttg    3780
acctgtatcc tttatttaca tgggtttttt ctttcgtagt tttggttttt cactcctgtc    3840
cagtctattt attattcaaa taggaaaaat tactttacag gttgttttac tgtagcttat    3900
aatgatactg tagttattcc agttactagt ttactgtcag agggctgcct ttttcagata    3960
aatattgaca taataactga agttattttt ataagaaaat caagtatata aatctaggaa    4020
agggatcttc tagtttctgt gttgtttaga ctcaaagaat cacaaatttg tcagtaacat    4080
gtagttgttt agttataatt cagagtgtac agaatggtaa aaattccaat cagtcaaaag    4140
aggtcaatga attaaaaggc ttgcaacttt ttcaaaaacc tgttagaata tgc           4193
```

<210> SEQ ID NO 3
<211> LENGTH: 19
<212> TYPE: RNA
<213> ORGANISM: Artificial
<220> FEATURE:
<223> OTHER INFORMATION: siRNA specific for DNAJC10

<400> SEQUENCE: 3
guaagaaugc uuugccgaa                                                    19

<210> SEQ ID NO 4
<211> LENGTH: 19
<212> TYPE: RNA
<213> ORGANISM: Artificial
<220> FEATURE:
<223> OTHER INFORMATION: siRNA specific for DNAJC10

<400> SEQUENCE: 4
gcuggaacua uuaucguua                                                    19

<210> SEQ ID NO 5
<211> LENGTH: 19
<212> TYPE: RNA
<213> ORGANISM: Artificial
<220> FEATURE:
<223> OTHER INFORMATION: siRNA specific for DNAJC10

<400> SEQUENCE: 5
gcagcauguu agaaguaca                                                    19

<210> SEQ ID NO 6
<211> LENGTH: 19
<212> TYPE: RNA
<213> ORGANISM: Artificial
<220> FEATURE:
<223> OTHER INFORMATION: siRNA specific for DNAJC10

<400> SEQUENCE: 6
cuaaagaagu ggauggguu                                                    19

US 7,928,084 B2

REGULATION OF INTEGRIN SURFACE EXPRESSION

CROSS REFERENCE TO RELATED APPLICATIONS

This application claims priority to U.S. Provisional Patent Application No. 61/090,488, filed on Aug. 20, 2008, which is incorporated by reference herein in its entirety.

REFERENCE TO GOVERNMENT

This invention was made with Government support under Grant No. K08 HL68622 01 awarded by NIH NHLBI. The Government has certain rights in this invention.

REFERENCE TO SEQUENCE LISTINGS TABLES OR COMPUTER PROGRAM LISTING

A Sequence Listing is included herein.

BACKGROUND OF THE INVENTION

Platelets play a central role in hemostasis and thrombosis, initiating clot formation in response to vessel wall damage. Platelets can also form pathological thrombus and the resulting arterial occlusion can lead to myocardial infarction or stroke. The platelet membrane glycoprotein αIIbβ3 (also called GPIIbIIIa) complex is a member of the integrin family of adhesion receptors. The αIIbβ3 glycoprotein plays a critical role in platelet aggregation, a process that requires the agonist-induced binding of fibrinogen to αIIbβ3. Agonists activate αIIbβ3, presumably by inducing a conformational change that exposes a binding site for fibrinogen, thus enabling fibrinogen to bind in a calcium-dependent manner. Once fibrinogen is bound, platelets can aggregate.

The platelet surface receptor αIIbβ3 is a known therapeutic target and αIIbβ3 agonists are used as therapeutic agents. Antagonists of αIIbβ3 can halt, or even reverse, the progression of nascent thrombus formation in both the coronary and cerebral circulations, particularly when administered intraarterially. Very early use of αIIbβ3 antagonists can also induce coronary artery reperfusion in patients with acute myocardial infarction. Currently available αIIbβ3 antagonists target the fibrinogen binding site on αIIbβ3. However, current anti-αIIbβ3 agents can cause fatal hemorrhage and attempts to develop oral αIIbβ3 antagonists have failed due to lack of efficacy, increased hemorrhage, thrombocytopenia and an increase in mortality. It has been hypothesized that these oral agents caused conformational changes in αIIbβ3 that resemble receptor activation. Therefore, development of oral αIIbβ3 antagonists that do not induce the active conformation of the receptor will have advantages over the currently available agents.

In light of this, compositions and methods that modify post-translational processing and trafficking of αIIbβ3 in the megakaryocyte, would overcome the shortcomings of currently available therapeutic agents, and would therefore be desirable.

SUMMARY OF THE INVENTION

This disclosure relates to altering the expression of the integrin αIIbβ3 on the surface of megakaryocytes by modifying the interaction between DNAJC10 and αIIbβ3 within the megakaryocyte.

In one embodiment disclosed herein, a method of preventing or treating a condition associated with platelet aggregation is provided. The method comprises administering a therapeutically effective amount of a composition that modifies the interaction of DNAJC10 with αIIbβ3 in a megakaryocyte.

In another embodiment, is a method of preventing or treating atherosclerosis by administering a therapeutically effective amount of a composition that modifies the interaction of DNAJC10 with αIIbβ3 in a megakaryocyte.

In yet another embodiment, a method of preventing or treating thrombosis is provided. The method comprises administering a therapeutically effective amount of a composition that modifies the interaction of DNAJC10 with αIIbβ3 in a megakaryocyte.

In another embodiment, a composition for preventing or treating a condition associated with platelet aggregation is provided. The composition comprises a therapeutically effective amount of a pharmacologically active agent and a carrier, wherein the active agent augments the interaction between DNAJC10 with αIIbβ3 in a megakaryocyte. In another embodiment, the pharmacologically active agent inhibits the interaction between DNAJC10 with αIIbβ3 in a megakaryocyte.

BRIEF DESCRIPTION OF THE DRAWINGS

FIG. 2 depicts RNAi-mediated knockdown of the ER protein DNAJC10 leading to increased αIIbβ3 surface expression on megakaryocytes.

FIG. 3 depicts the expression of αIIbβ3 on HEK 293 cells after siRNA knockdown of calnexin cycle proteins.

DETAILED DESCRIPTION OF THE INVENTION

The present disclosure relates to altering the expression of the integrin αIIbβ3 on the surface of megakaryocytes and platelets by modifying its interaction with the endoplasmic reticulum (ER) protein DNAJC10. The interaction of αIIbβ3 with DNAJC10 provides a novel therapeutic target for intervention to increase or decrease αIIbβ3 expression on platelets and therefore alter platelet aggregation.

Figure 1:
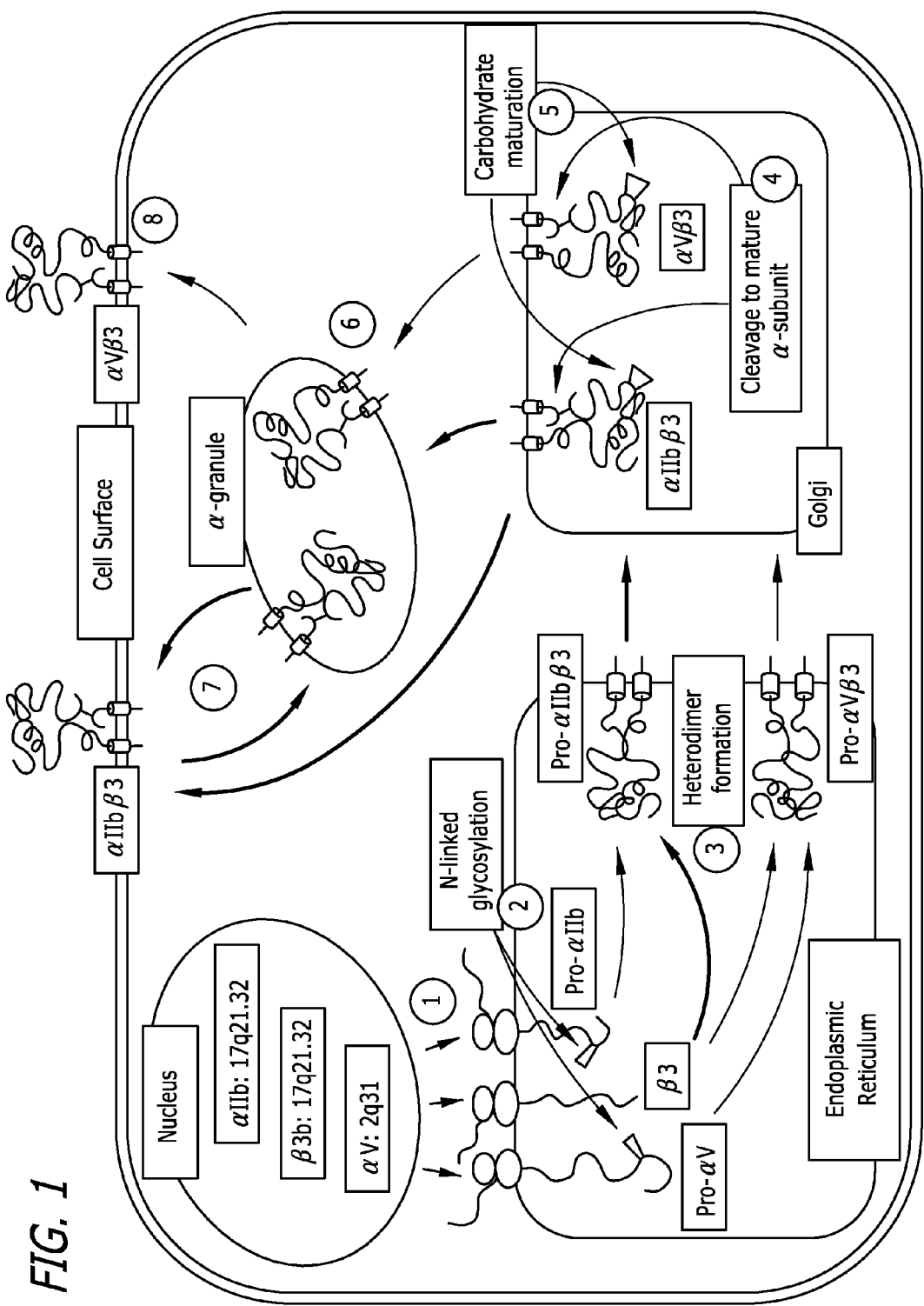
FIG. 1 is a schematic depicting the current model of platelet integrin processing and maturation. Without wishing to be bound by any particular theory, it is thought that nascent pro-αIIb, αv and β3 subunits enter the lumen of the endoplasmic reticulum cotranslationally through translocon pores (1). Glycosylation and disulfide-bond formation occurs on both subunits (2). The subunits associate to form pro-αIIbβ3 and pro-αvβ3 complexes that are transported to the Golgi (3). Pro-αIIbβ3 and pro-αvβ3 subunits are synthesized as single-chain precursors and are cleaved by furin in the Golgi to two-chain molecules that remain associated by a disulfide-bond (4). The pro-αIIb, αv and β3 subunits undergo additional oligosaccharide processing in the Golgi (5). The mature complexes are transported to the alpha granules (6), and from there to the cell surface. The mature complexes cycle between the platelet surface and alpha granules (7 and 8).
Figure 2A:
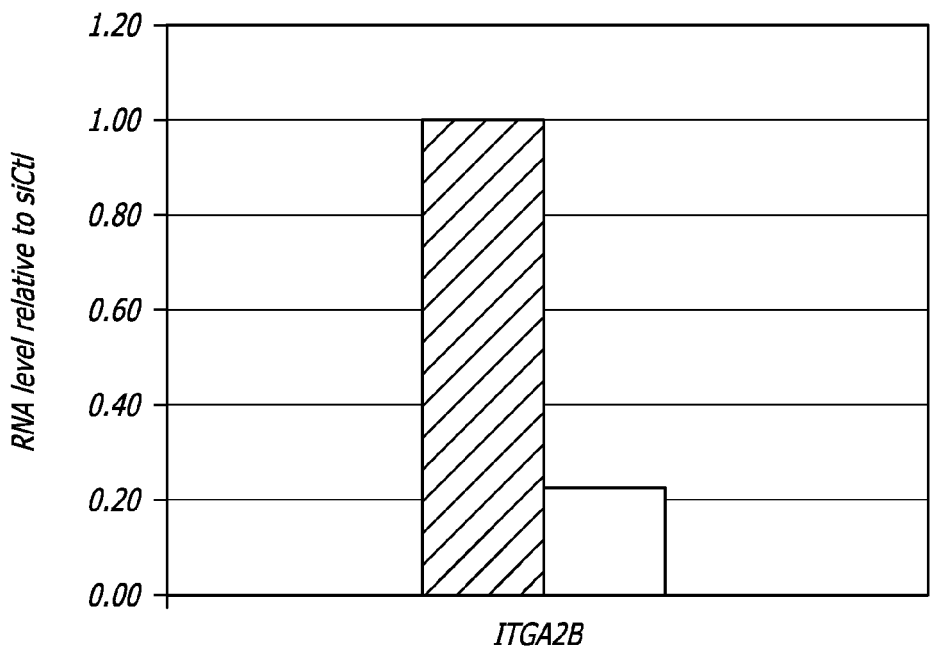
FIGS. 2A and 2B depict quantitative RT-PCR demonstrating fold decreases of αIIb and DNAJC10 mRNA levels after transfection with anti-αIIb (FIG. 2A) or anti-DNAJC10 (FIG. 2B) siRNA, respectively.
Figure 2B:
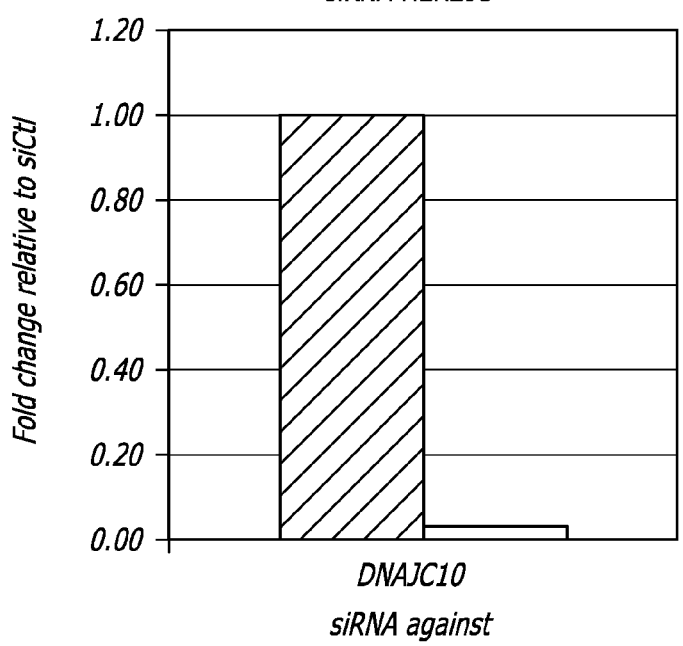
Figure 2C:
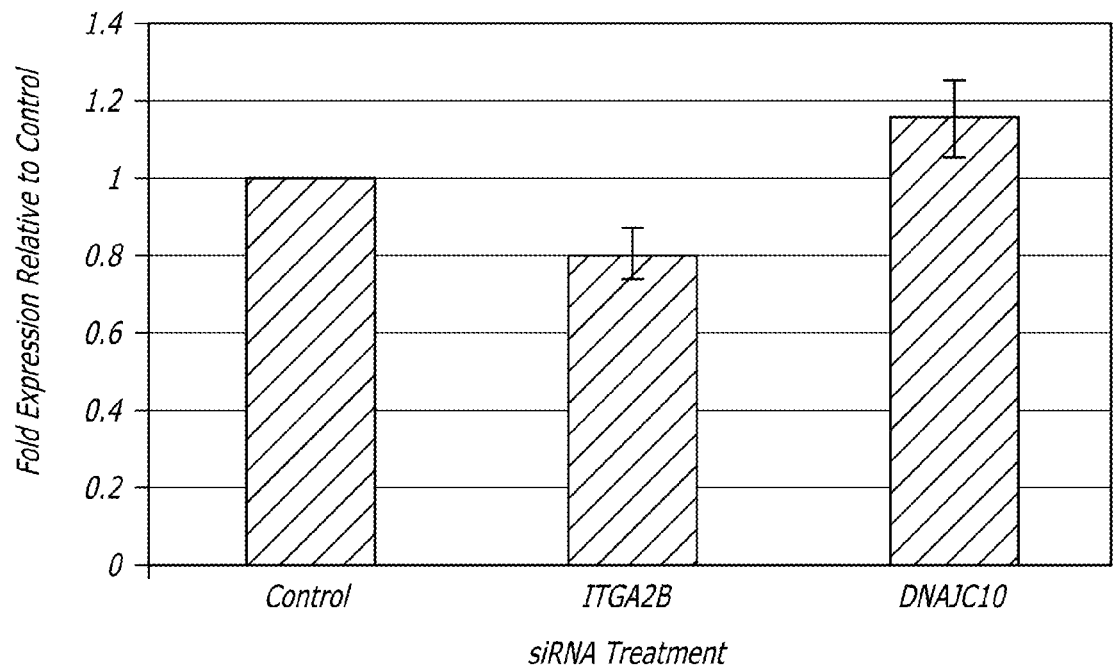
FIG. 2C depicts surface expression of αIIbβ3, as measured by binding of monoclonal antibody 10E5 on megakaryocytes after treatment with siRNA against αIIb or DNAJC10. Surface expression of αIIbβ3 was decreased 20% by anti-αIIb siRNA, and increased 15% by DNAJC10 siRNA.
Figure 2D:
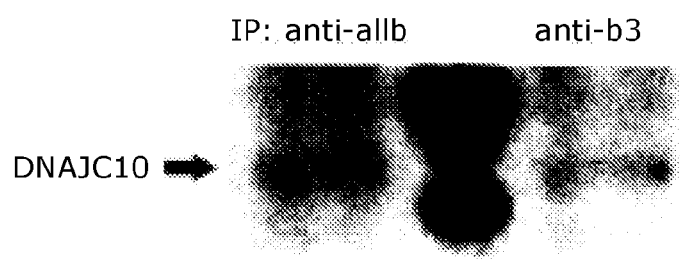
FIG. 2D depicts DNAJC10 co-immunoprecipitated with αIIb and β3 from whole cell lysates of megakaryocytes, indicating a physical interaction between αIIb, β3 and DNAJC10.

The current model of platelet integrin processing and maturation is shown in FIG. 1. Without wishing to be bound by any particular theory, it is thought that the formation of integrin receptors occurs in the calcium-rich environment of the ER where nascent α- and β-subunits are independently expressed and assembled into heterodimeric complexes. Receptor complexes that are properly folded are exported from the ER to the Golgi where they undergo further oligosaccharide processing and maturation. The mature complexes are transported to the alpha granules and then to the cell surface (FIG. 1).

The heat shock protein known as DNAJC10 is expressed in secretory cells in response to cell stress and interacts with BiP, an endoplasmic reticulum chaperone protein, and EDEM, part of the protein degradation machinery in the endoplasmic reticulum.

In the ER of megakaryocytes, DNAJC10 interacts with αIIbβ3 as demonstrated by co-immunoprecipitation using anti-αIIb and anti-β3 antibodies. Decreasing the mRNA levels of DNAJC10 in megakaryocytes results in a significant increase in the number of αIIbβ3 receptors on the cell surface. Increasing or decreasing the number or function of DNAJC10 molecules represents a novel therapeutic approach to increasing or decreasing αIIbβ3 surface expression on platelets.

The instant disclosure contemplates both increasing and decreasing platelet surface expression of αIIbβ3. In one embodiment, a method is provided for preventing or treating a condition associated with platelet aggregation, comprising administering a therapeutically effective amount of a composition that modifies the interaction between DNAJC10 and αIIbβ3 in a megakaryocyte.

In one embodiment, αIIbβ3 surface expression is increased by inhibiting DNAJC10 interaction with αIIbβ3 by means including, but not limited to, a small molecule inhibitor of DNAJC10, by sequestration or deactivation of DNAJC10 by chemical modification, and use of a decoy substrate which competes with αIIbβ3 for DNAJC10. In another embodiment, αIIbβ3 surface expression is increased by a decreased interaction of DNAJC10 with its substrates by decreasing the production of DNAJC10 using antisense or RNAi technology (e.g., siRNA, shRNA, miRNA), delivered by viral vector or other means. In one embodiment, the antisense or RNAi is delivered using a megakaryocyte-specific promoter. Additionally, specific inhibitors or antagonists, or targeted destruction techniques may be used to decrease levels of DNAJC10 and therefore inhibit its interaction with αIIbβ3. These techniques and others described herein are well known in the art.

In another embodiment, αIIbβ3 surface expression is decreased by augmenting the effects of DNAJC10 on αIIbβ3 surface expression. In one embodiment, this is achieved using a small molecule mimetic that performs the same function as DNAJC10. In another embodiment, αIIbβ3 surface expression is decreased by increasing the apparent activity of DNAJC10 by increasing the transcription of DNAJC10 or by increasing the function and/or stability of DNAJC10 and/or molecular partners of DNAJC10 (such as, but not limited to BiP, HSP60, HSP90-1alpha, AMP-activated kinase, HSC70, heterogenous nuclear ribonucleoprotein H1, tubulin beta-1 chain, mitogen-activated protein kinase7 interacting protein, mortalin, filamin A, and combinations thereof). In another embodiment, αIIbβ3 surface expression is decreased by increasing the level of DNAJC10 expression such as by using gene therapy targeted for megakaryocyte production with a megakaryocyte-specific promoter.

The disclosure further provides a composition to modify the interaction of DNAJC10 and αIIbβ3. The composition comprises a pharmacologically active agent capable of augmenting or inhibiting the interaction between DNAJC10 and αIIbβ3. The pharmacologically active agent may inhibit or augment the interaction by one or more of the mechanisms described above.

The pharmacologically active agent can be any combination of amino acids, protein, peptide, fragment, and nucleic acid that increases or decreases the expression or function of DNAJC10 or of a protein or molecular partner that affects the stability and function of DNAJC10.

Accordingly, included within the scope of the present disclosure are insertion, deletion or conservative amino acid substitution variants of DNAJC10 (SEQ ID NO: 1). As used herein, a conservative variant refers to alterations in the amino acid sequence that do not adversely affect the biological functions of the protein. A substitution, insertion or deletion is said to adversely affect the protein when the altered sequence prevents or disrupts a biological function associated with the protein. For example, the overall charge, structure or hydrophobic/hydrophilic properties of the protein, in certain instances, may be altered without adversely affecting a biological activity. Accordingly, the amino acid sequence can be altered, for example to render the peptide more hydrophobic or hydrophilic, without adversely affecting the biological activities of the protein.

Ordinarily, the allelic variants, the conservative substitution variants, and the members of the protein family, will have an amino acid sequence having at least about 50%, 60%, 70% or 75% amino acid sequence identity with DNAJC10, more preferably at least about 80-90%, even more preferably at least about 92-94%, and most preferably at least about 95%, 98% or 99% sequence identity. Identity or homology with respect to such sequences is defined herein as the percentage of amino acid residues in the candidate sequence that are identical with DNAJC10, after aligning the sequences and introducing gaps, if necessary, to achieve the maximum percent homology, and not considering any conservative substitutions as part of the sequence identity (see section B for the relevant parameters). Fusion proteins, or N-terminal, C-terminal or internal extensions, deletions, or insertions into the peptide sequence shall not be construed as affecting homology.

Thus, the proteins disclosed herein include molecules having the amino acid sequence of DNAJC10; fragments thereof having a consecutive sequence of at least about 3, 4, 5, 6, 10, 15, 20, 25, 30, 35 or more amino acid residues of these proteins; amino acid sequence variants wherein one or more amino acid residues has been inserted N- or C-terminal to, or within, the disclosed coding sequence; and amino acid sequence variants of the disclosed sequence, or their fragments as defined above, that have been substituted by at least one residue. Such fragments, also referred to as peptides or polypeptides, may contain antigenic regions, functional regions of the protein identified as regions of the amino acid sequence which correspond to known protein domains, as well as regions of pronounced hydrophilicity. The regions are all easily identifiable by using commonly available protein sequence analysis software such as MacVector (Oxford Molecular).

Contemplated variants further include those containing predetermined mutations by, e.g., homologous recombination, site-directed or PCR mutagenesis, and the corresponding proteins of other animal species, including but not limited to rabbit, mouse, rat, porcine, bovine, ovine, equine and non-human primate species, and the alleles or other naturally occurring variants of the family of proteins; and derivatives wherein the protein has been covalently modified by substitution, chemical, enzymatic, or other appropriate means with a moiety other than a naturally occurring amino acid (for example a detectable moiety such as an enzyme or radioisotope).

The present disclosure further provides compositions comprising a protein or polypeptide of DNAJC10 and a diluent. Suitable diluents can be aqueous or non-aqueous solvents or a combination thereof, and can comprise additional components, for example water-soluble salts or glycerol, that contribute to the stability, solubility, activity, and/or storage of the protein or polypeptide.

The present disclosure further provides nucleic acid molecules that encode the protein of DNAJC10 and the related proteins herein described, preferably in isolated form. As used herein, "nucleic acid" is defined as RNA or DNA that encodes a protein or peptide as defined above, is complementary to a nucleic acid sequence encoding such peptides, hybridizes to the nucleic acid of such proteins or peptides and remains stably bound to it under appropriate stringency conditions, encodes a polypeptide sharing at least about 50%, 60%, 70% or 75%, preferably at least about 80-90%, more preferably at least about 92-94%, and most preferably at least about 95%, 98%, 99% or more identity with the peptide sequence of DNAJC10 or exhibits at least 50%, 60%, 70% or 75%, preferably at least about 80-90%, more preferably at least about 92-94%, and even more preferably at least about 95%, 98%, 99% or more nucleotide sequence identity over the open reading frames of the DNAJC10 gene.

Specifically contemplated are genomic DNA, cDNA, mRNA and antisense or RNAi (e.g., siRNA, miRNA, shRNA, etc.) molecules, as well as nucleic acids based on alternative backbones or including alternative bases, whether derived from natural sources or synthesized. Such hybridizing or complementary nucleic acids, however, are defined further as being novel and unobvious over any prior art nucleic acid including that which encodes, hybridizes under appropriate stringency conditions, or is complementary to nucleic acid encoding a protein according to the present disclosure.

Homology or identity at the nucleotide or amino acid sequence level is determined by BLAST (Basic Local Alignment Search Tool) analysis using the algorithm employed by the programs blastp, blastn, blastx, tblastn and tblastx which are tailored for sequence similarity searching. The approach used by the BLAST program is to first consider similar segments, with and without gaps, between a query sequence and a database sequence, then to evaluate the statistical significance of all matches that are identified and finally to summarize only those matches which satisfy a preselected threshold of significance. The search parameters for histogram, descriptions, alignments, expect (i.e., the statistical significance threshold for reporting matches against database sequences), cutoff, matrix and filter (low complexity) are at the default settings. The default scoring matrix used by blastp, blastx, tblastn, and tblastx is the BLOSUM62 matrix, recommended for query sequences over 85 nucleotides or amino acids in length.

For blastn, the scoring matrix is set by the ratios of M (i.e., the reward score for a pair of matching residues) to N (i.e., the penalty score for mismatching residues), wherein the default values for M and N are 5 and −4, respectively. Four blastn parameters were adjusted as follows: Q=10 (gap creation penalty); R=10 (gap extension penalty); wink=1 (generates word hits at every wink$^{th}$ position along the query); and gapw-16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

"Stringent conditions" are those that (1) employ low ionic strength and high temperature for washing, for example, 0.015 M NaCl/0.0015 M sodium citrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal. Preferred molecules are those that hybridize under the above conditions to the complement of the sequence of DNAJC10 and which encode a functional or full-length protein. Even more preferred hybridizing molecules are those that hybridize under the above conditions to the complement strand of the open reading frame of the sequence of DNAJC10.

As used herein, a nucleic acid molecule is said to be "isolated" when the nucleic acid molecule is substantially separated from contaminant nucleic acid molecules encoding other polypeptides.

The present disclosure further provides fragments of the disclosed nucleic acid molecules. As used herein, a fragment of a nucleic acid molecule refers to a small portion of the coding or non-coding sequence. The size of the fragment will be determined by the intended use. For example, if the fragment is chosen so as to encode an active portion of the protein, the fragment will need to be large enough to encode the functional region(s) of the protein. For instance, fragments which encode peptides corresponding to predicted antigenic regions may be prepared. If the fragment is to be used as a nucleic acid probe or PCR primer, then the fragment length is chosen so as to obtain a relatively small number of false positives during probing/priming.

The pharmacologically active agent in the composition can be provided alone, or in combination with other agents that modify the interaction of DNAJC10 and αIIbβ3. For example, an agent can be administered in combination with other known drugs. As used herein, two agents are said to be administered in combination when the two agents are administered simultaneously or are administered independently in a fashion such that the agents will act at the same time.

The agent can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The present disclosure further provides compositions containing one or more agents which modulate expression or at least one activity of a protein or gene. While individual needs vary, determination of optimal ranges of effective amounts of each component is within the skill of the art. Typical dosages comprise 0.1 to 100 µg/kg body wt. The preferred dosages comprise 0.1 to 10 µg/kg body wt. The most preferred dosages comprise 0.1 to 1 µg/kg body wt.

The composition can be administered at any suitable time to achieve the desired result, that is, to prevent or treat a condition associated with platelet aggregation. In this regard, the composition may be administered prior to the onset of the condition, at the onset of the condition, or some time after the onset of the condition. Alternately, any combination of approaches may be utilized to prevent and/or treat the condition. For example, the composition may be administered at the onset of the condition and may be administered for a period of hours, days, weeks, or months thereafter. The composition may be administered on an in-patient or out-patient basis as determined by the administering physician. In one embodiment, the composition may be administered during a medical procedure in order to prevent and/or treat a condition associated with platelet aggregation. Non-limiting examples of such medical procedures include an angiogram, angioplasty, catheterization, placement of a filter for deep vein thrombosis, intra-arterial stent placement, and combinations thereof.

In addition to the pharmacologically active agent, the compositions disclosed herein may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration may be formulated for enteral or parenteral administration. Indeed, both types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods disclosed herein, the compounds may be used alone or in combination, or in combination with other therapeutic or diagnostic agents. The composition of this invention may be coadministered along with other compounds/compositions typically prescribed for these conditions according to generally accepted medical practice. The composition can be utilized in vivo, ordinarily in mammals, such as humans, sheep, horses, cattle, pigs, dogs, cats, rats and mice, or in vitro.

A variety of diseases and conditions can be prevented and/or treated by modulating expression of DNAJC10 and/or αIIbβ3. Non-limiting examples of these diseases include:

Glanzmann thrombasthenia: Individuals with this inherited disorder have little or no functional αIIbβ3 on their platelets and have a lifelong bleeding diathesis. Therapy is limited to platelet transfusion and activated Factor VII. The only cure is bone marrow transplant which carries significant risks. These individuals are also likely to develop antibodies against platelets, which severely reduces their treatment options. In these patients, a therapeutic intervention that results in the increased expression of their endogenous αIIbβ3 could be clinically effective, would decrease the patient's exposure to blood products and could possibly be used for prophylaxis.

Pathological thrombosis: Platelet-mediated thrombosis is a causative factor in coronary artery thrombosis and myocardial infarction, mortality after post-percutaneous stent placement, stent re-stenosis, formation of atherosclerotic lesions, pulmonary embolism, deep vein thrombosis, and thrombotic and embolic stroke.

Platelet activation in sickle cell disease: Individuals with sickle cell anemia are known to have increased numbers of circulating platelets and an increased percentage of activated platelets. These activated platelets are thought to play a role in the pathophysiology of arterial disease and organ damage in these individuals.

Diseases associated with integrins: Integrins are a large family of surface adhesion and signaling receptors and are implicated in many physiological processes and many disease states. Integrin deficiencies are known to cause Glanzmann thrombasthenia and Leukocyte Adhesion Deficiency, an immune deficiency disease. To date, anti-integrin therapy has been used to treat complications of arterial thrombosis and of integrin-mediated inflammation in multiple sclerosis and Crohn's disease.

Cancer: DNAJC10 is part of a stress-response mechanism, present in all cells, called the Unfolded Protein Response (UPR), which protects cells against a build-up of misfolded or aggregated proteins. In cancer cells, in which DNAJC10 expression is increased, the UPR is unusually active as compared to normal cells. Inhibition of the UPR can be fatal to cancer cells, while normal cells may be unaffected. For example, the heat shock protein HSP90 is a stress response protein that interacts with a multitude of nascent proteins and either stabilizes them and assists their folding or directs them to the proteasome for degradation to clear the way for new proteins. Inhibitors of HSP90 exploit the fact that normal cells can compensate for the loss of HSP90, while cancerous cells cannot, and have been very successful in treating hematologic and solid malignancies. There are a large number of proteins involved in the UPR, but their individual roles are mostly unknown.

Conformational diseases: Many inherited diseases derive some or all of their pathophysiology from defective protein processing, rather than defective protein function. Gaucher and Fabry diseases are multisystem metabolic diseases resulting from defects of specific carbohydrate processing enzymes. The defective enzymes appear to have enzymatic activity, but their mutations cause them to be recognized and destroyed by the cells' quality control mechanisms. Hence, they may be termed "conformational diseases" because the pathology results from the defective conformation of the enzyme, not defective function. Both diseases are now being successfully treated with small molecule chaperone therapy. These molecules bind to the active sites of the nascent (defective) enzymes during synthesis, stabilizing and protecting them so that they can be sorted and delivered to their appropriate locations, where they can perform their normal functions.

Disseminated intravascular coagulation (DIC): DIC is a disorder in which proteins that control blood clotting become abnormally active. The disorder can result in a plurality of clots throughout the body, but more commonly, severe bleeding as clotting proteins become depleted. Treatment includes blood transfusions and medications that control blood clotting.

EXAMPLES

The following materials and methods are used throughout the examples that follow.

Human megakaryocyte-lineage cells that did not meet criteria for clinical use and were designated for research use or destruction by informed consent in accordance with the declaration of Helsinki are obtained from the National Cord Blood Program. Leukocytes were separated by Dextran 70 sedimentation, and then enriched for CD34+ progenitor cells by negative selection using a combination of antibodies against maturation/lineage-specific markers (RosetteSep, StemCell Technologies, Vancouver, BC) concomitant with density sedimentation using Ficoll-Paque Plus. Cells were cultured in serum-free medium (StemSpan medium, StemCell Technologies) with 50 ng/ml thrombopoietin, 1 ng/ml stem cell factor, and penicillin/streptomycin.

HEK293 cell lines that stably expressed human αIIbβ3 receptor were established by transfection with Lipofectamine 2000, followed by selection in media containing 500 µg/ml G418 for 2-4 weeks, followed by FACS sorting (MoFlo cell sorter, Beckman Coulter, Fullerton, Calif.) for high binding of the anti-αIIbβ3 mAb, 10E5. HEK293 cells stably expressing αIIb only, or mutant αIIb β3 that is not expressed on the surface, can not be sorted by FACS and instead were cultured continuously in G418. Since HEK293 cells express very low levels of avb3, cells transfected with β3 express very low levels of avb3 on the surface, and were sorted by FACS using an anti-avb3 mAb, LM609.

Cells for mass spectrometry, immunoprecipitation, and immunoblotting were lysed in 1% Brij 98 or 1% Triton-x lysis buffer containing protease inhibitors and 20 uM NEM (to preserve disulfide bond structure). Lysates were precleared with protein-G Sepharose beads, and then equivalent amounts of protein were incubated 3-16 h at 4° C. with one or more antibody (4 µg/reaction). Samples were incubated with protein-G Sepharose beads for one h at 4° C., washed twice, and incubated with SDS sample buffer for 10 min at 100° C. Some samples were reduced with 10% beta mercaptoethanol. Proteins were separated by SDS-PAGE, and the gels were either stained with Coomassie for mass spectrometry or transferred to PVDF membranes for immunoblotting. The amount of each mAb used for immunoprecipitation was determined to be at a near-saturating concentration by titration experiments using 0 to 20 µg of each mAb. Non-specific binding was determined by performing parallel immunoprecipitation with the appropriate mouse or rabbit immunoglobulin in each experiment, a very important control since the chaperone proteins tend to bind to both antibodies and Sepharose beads.

Cells for biosynthetic labeling and immunoprecipitation were incubated for 30 min at 37° C. in methionine/cysteine-free medium, followed by pulse-labeling for 15 min at 37° C. in medium containing $^{35}$S-methionine/cysteine (300 µCi/10 cm plate). The pulse was terminated by incubation in medium containing excess unlabeled methionine/cysteine (1 mg/ml each) and the cells were incubated at 37° C. until lysis in 1% Triton-X 100 lysis buffer. Precleared lysates containing equivalent amounts of trichloroacetic acid-precipitable radioactivity were, as described above, subjected to SDS-PAGE, and then the gels were dried and exposed to film.

Quantitative RT-PCR for analysis of RNA content. Cells were collected in RNAlater (Applied Biosystems, Carlsbad, Calif.) RNA stabilization solution and RNA extracted with the RNEasy kit (Qiagen, Valencia, Calif.). Analysis was performed on an ABI 7300 thermocycler/fluorescence analyzer (Applied Biosystems, Carlsbad, Calif.) using the SYBR green probe (Qiagen, Valencia, Calif. or Invitrogen, Carlsbad, Calif.) and Quantitect primer assays (Qiagen, Valencia, Calif.). Relative mRNA levels were calculated using the ΔΔCt method which corrects for GAPDH expression in all samples and determines fold-change in RNA level relative to a control sample.

Example 1

Isolation of Megakaryocytes

Units of umbilical cord blood (UCB) not suitable for clinical use were obtained from the National Cord Blood Program. CD34+ progenitor cells were isolated by negative selection using a combination of antibodies against maturation/lineage-specific markers (ROSETTESEP, Stem Cell Technologies) concomitant with Ficoll-Paque Plus density sedimentation. Optimal culture conditions for obtaining high yields of megakaryocyte-lineage cells in serum-free medium (SFEM, Stem Cell Technologies) were established by varying the cell and cytokine concentrations. Cells were plated at $1 \times 10^6$ cells/ml and grown in 50 ng/ml thrombopoietin (TPO) and 1 ng/ml stem cell factor (SCF). After 8-10 days of culture, a single population of large cells remained, of which 95±2% expressed αIIbβ3, 83±5% expressed GPIb and 54±10% expressed α2β1 (mean±SD, all n=4). Upon incubation with 10 mM thrombin receptor-activating peptide, the percentage of UCB cells recognized by PAC1, an activation-dependent, ligand-mimetic anti-αIIbβ3 monoclonal antibody, increased from 3±2% to 16±1% (n=3). The megakaryocytes started elaborating proplatelets after 8-9 days.

Example 2

Identification of DNAJC10 as an αIIbβ3 Interacting Protein

Mass spectroscopy was used to identify proteins that interact with αIIb and β3 in both HEK293 cells and stem cell-derived megakaryocytes. Two methods were used for capturing interacting proteins: 1) a two cell pull-down assay using histidine-tagged αIIb and β3 as bait, and 2) incorporation of photoreactive, cross-linking amino acids into growing megakaryocytes, followed by immunoprecipitation of αIIb and β3. Proteins isolated by each technique were separated on SDS-PAGE and analyzed by mass spectrometry. These assays identified DNAJC10 as an interacting protein with αIIbβ3.

Direct interaction of DNAJC10 with αIIbβ3 was confirmed by co-immunoprecipitation. Whole cell lysates of HEK293 cells or UCB-derived megakaryocytes were subjected to immunoprecipitation with monoclonal antibodies against αIIb or β3, the antibodies were adsorbed onto protein G beads and then the immunoprecipitated proteins were subjected to SDS-PAGE. The proteins were transferred to PVDF membranes and immunoblotted with anti-DNAJC10 antibodies, which demonstrated the presence of DNAJC10 which had co-immunoprecipitated with αIIb and β3 in both HEK293 cells and megakaryocytes.

Example 3

Knockdown of DNAJC10 mRNA Results in Increased αIIbβ3 Surface Expression on Megakaryocytes Small interfering RNA (siRNA) (SEQ ID NOs: 2-5) was used to knock down DNAJC10 mRNA (SEQ ID NO: 6) in UCB-derived megakaryocytes. Knockdown of DNAJC10 resulted in a 15% increase in αIIbβ3 surface expression as compared to controls (FIGS. 2A-D). These results indicate that the DNAJC10 protein plays a role in αIIbβ3 trafficking to the megakaryocyte surface.

Example 4

Preliminary studies showed that 400 nM siRNA (SEQ ID NOs: 2-5) duplexes transfected on days 4 and 6 of UCB culture resulted in 40%-50% transfection efficiency, as judged by either co-transfection of a GFP-labeled non-targeting siRNA duplex or a Cy3-labeled experimental siRNA duplex. The amount of DHARMAFECT 1 reagent (Thermo Scientific, Waltham, Mass.) was also optimized for lowest toxicity with highest transfection efficiency. Transfection efficiency was measured by flow cytometry. The effect of the experimental siRNA duplexes was determined by comparing the αIIbβ3 expression level, as judged by 10E5 binding, between the experimental and control cells. Only fluorescently labeled cells were gated and compared to each other. The functionality of the siRNA duplexes was determined by quantitative RT-PCR, which was performed on an ABI 7300 real-time fluorescence analyzer. SYBR Green dye (Molecular Probes, Carlsbad, Calif.) was used as the labeling dye. Sequencing primers were predesigned from Qiagen. Data was analyzed using the ΔΔCt method with GAPDH as a loading control. Initial experiments were done using HEK293 cells stably expressing αIIbβ3, since the transfection efficiency was reliably >70% after one transfection with Dharmafect 1 reagent and 100 nM pooled siRNA duplexes (Thermo Scientific).

Figure 3A:
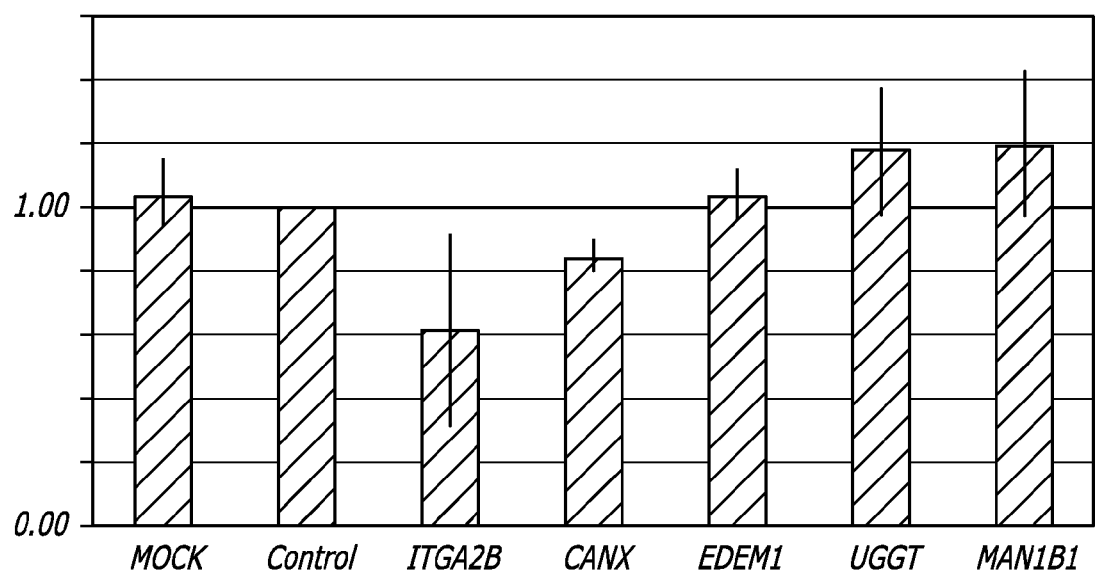
FIG. 3A shows fold-change in the MFI (mean fluorescence intensity, a measure of the amount of antibody bound onto the cell surface)±CI (95% confidence interval) of the anti-αIIbβ3 mAb 10E5 after siRNA mediated knockdown of calnexin cycle proteins.
Figure 3B:
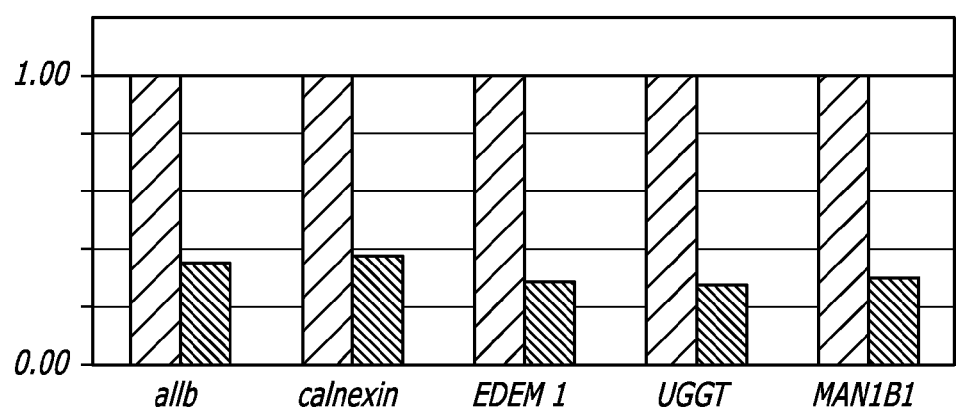
FIG. 3B shows the fold-decrease of mRNA level after siRNA treatment. Correcting for approximately 70% transfection efficiency, this is >90% increase.

For preliminary analysis, proteins were chosen from the calnexin cycle of protein quality control, since αIIb was previously shown to engage this cycle. siRNA against αIIb itself, and against calnexin decreased αIIbβ3 surface expression on HEK293 cells (FIGS. 3A-B). However, siRNA against other enzymes in the calnexin cycle did not significantly alter αIIbβ3 expression. This was not surprising since the calnexin cycle is a quality control mechanism that operates to retain and degrade proteins, rather than to maximize their expression. However, the finding that depletion of calnexin mRNA resulted in decreased αIIbβ3 surface expression supports a previous finding that the interaction of the αIIb N15 glycan with calnexin was important for αIIbβ3 complex formation. mRNA was prepared from the HEK293 cells and analyzed as described above. The efficacy of the siRNA knockdown was >90% after correction for transfection efficiency.

Figure 4A:
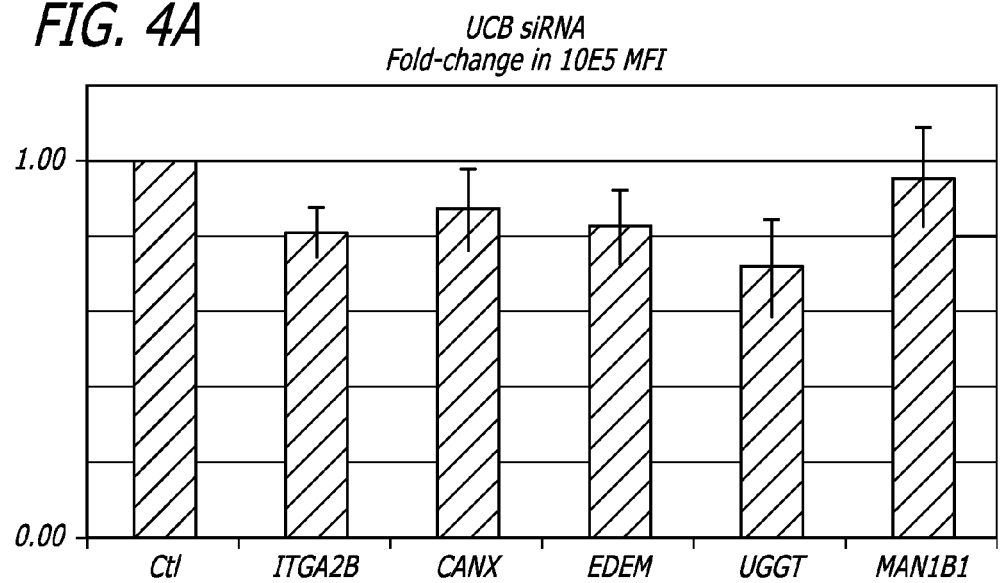
FIG. 4 depicts the expression of αIIbβ3 on UCB derived megakaryocytes after siRNA knockdown of calnexin cycle proteins. The fold-change (FIG. 4A) in MFI±CI of the anti-αIIbβ3 mAb 10E5 after siRNA mediated knockdown of calnexin cycle proteins is shown. The fold-decrease of mRNA level after siRNA treatment is shown in FIG. 4B. Correcting for approximately 50% transfection efficiency, this is >80% decrease.
Figure 4B:
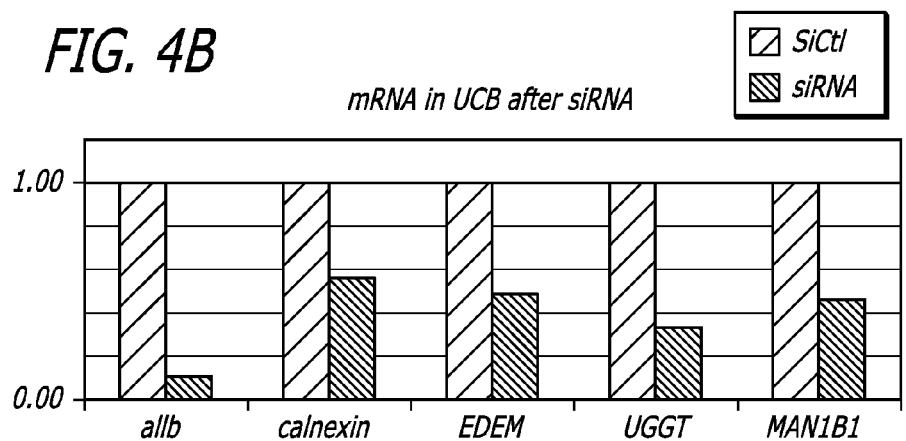

Next, UCB derived megakaryocytes were transfected with the same siRNA duplexes as described above. siRNA against αIIb, calnexin, EDEM1 and UGGT resulted in decreased αIIbβ3 expression on the megakaryocytes as judged by 10E5 binding (FIGS. 4A-B) To evaluate the efficacy of the siRNA duplexes in the UCB cells, QRTPCR was performed as described above, and corrected for a transfection efficiency of 50%.

Example 5

To identify the network of protein interactions involved in αIIb biogenesis, αIIb-containing protein complexes were isolated from UCB-derived megakaryocytes or from HEK293 cells expressing αIIbβ3, and these proteins were analyzed by mass spectrometry. A total of 123 proteins were identified in complex with mature αIIb by at least two peptides which had a Mascot score of at least 40, the minimal criteria for inclusion (Table 1). The primary data set of 123 proteins was augmented by including protein-protein interactions that were retrieved from public databases (NCBI, SWISSPROT, INTACT) using Cytoscape software (Yeung, *Curr. Protoc. Bioinformatics,* 8:813 (2008), Cline, *Nat. Protoc.,* 2:2366 (2007)). This protein network constitutes the αIIb interactome, a network of protein-protein interactions relevant to the trafficking and function of αIIb in megakaryocytes.

The Interactome of pro-αIIb. To enrich the capture assay for proteins which preferentially bind to pro-αIIb over mature αIIb, a poly-histidine tagged αIIb subunit harboring R858G and R859G mutations, which prevents pro-αIIb cleavage into mature αIIb (Kolodziej, *J. Biol. Chem.,* 266:23499 (1991)), was used as bait. A total of 102 proteins were identified in complex with pro-αIIb R858G/R859G by at least two peptides which had a Mascot score of at least 40, the minimal criteria for inclusion. This list of proteins differed from that identified using normal αIIb as bait, having about 16% overlap. However, like that derived from normal αIIb, this data set is also enriched for transport, ER and Golgi proteins, and nucleotide binding proteins (Table 1).

TABLE 1

Proteins Binding to αIIb

| Gene Symbol | # Peptides | No. Expts | Description |
|---|---|---|---|
| ITGA2B | 216 | 9 | INTEGRIN, ALPHA 2B (PLATELET GLYCOPROTEIN IIB OF IIB/IIIA COMPLEX, ANTIGEN CD41) |
| ITGB3 | 136 | 8 | INTEGRIN, BETA 3 (PLATELET GLYCOPROTEIN IIIA, ANTIGEN CD61) |
| GLUD1 | 83 | 3 | GLUTAMATE DEHYDROGENASE 1 |
| DHX15 | 68 | 2 | DEAH (ASP-GLU-ALA-HIS) BOX POLYPEPTIDE 15 |
| DARS | 65 | 4 | ASPARTYL-TRNA SYNTHETASE |
| KIAA1529 | 62 | 3 | KIAA1529 |

TABLE 1-continued

Proteins Binding to αIIb

| Gene Symbol | # Peptides | No. Expts | Description |
| --- | --- | --- | --- |
| TUBB | 52 | 2 | TUBULIN, BETA |
| TUBB2C | 36 | 1 | TUBULIN, BETA 2C |
| NT5DC2 | 34 | 2 | 5'-NUCLEOTIDASE DOMAIN CONTAINING 2 |
| NONO | 32 | 1 | NON-POU DOMAIN CONTAINING, OCTAMER-BINDING |
| DNMBP | 30 | 2 | DYNAMIN BINDING PROTEIN |
| KRT16 | 28 | 1 | KERATIN 16 (FOCAL NON-EPIDERMOLYTIC PALMOPLANTAR KERATODERMA) |
| HNRNPL | 26 | 2 | HETEROGENEOUS NUCLEAR RIBONUCLEOPROTEIN L |
| DHTKD1 | 25 | 1 | DEHYDROGENASE E1 AND TRANSKETOLASE DOMAIN CONTAINING 1 |
| PLG | 22 | 3 | PLASMINOGEN |
| CCT2 | 20 | 2 | CHAPERONIN CONTAINING TCP1, SUBUNIT 2 (BETA) |
| DPP9 | 20 | 1 | DIPEPTIDYL-PEPTIDASE 9 |
| ME2 | 20 | 1 | MALIC ENZYME 2, NAD(+)-DEPENDENT, MITOCHONDRIAL |
| TXNDC4 | 20 | 3 | THIOREDOXIN DOMAIN CONTAINING 4 (ENDOPLASMIC RETICULUM) |
| AKR7A2 | 19 | 1 | ALDO-KETO REDUCTASE FAMILY 7, MEMBER A2 (AFLATOXIN ALDEHYDE REDUCTASE) |
| DNAJC10 | 19 | 1 | DNAJ (HSP40) HOMOLOG, SUBFAMILY C, MEMBER 10 |
| HSPA5 | 19 | 1 | HEAT SHOCK 70 kDa PROTEIN 5 (GLUCOSE-REGULATED PROTEIN, 78 kDa) |
| ACTB | 18 | 2 | ACTIN, BETA |
| ALDH18A1 | 16 | 2 | ALDEHYDE DEHYDROGENASE 18 FAMILY, MEMBER A1 |
| LMAN1 | 16 | 1 | LECTIN, MANNOSE-BINDING, 1 |
| HSPA1A | 15 | 1 | HEAT SHOCK 70 kDa PROTEIN 1A |
| HSPA1B | 15 | 1 | HEAT SHOCK 70 kDa PROTEIN 1B |
| LOC731751 | 15 | 1 | UNKNOWN PROTEIN |
| FLNA | 14 | 2 | FILAMIN A, ALPHA (ACTIN BINDING PROTEIN 280) |
| TUBB4 | 14 | 1 | TUBULIN, BETA 4 |
| FARS2 | 13 | 1 | PHENYLALANINE-TRNA SYNTHETASE 2 |
| PKM2 | 13 | 1 | PYRUVATE KINASE, MUSCLE |
| PM20D2 | 13 | 1 | AMINOACYLASE 1-LIKE 2 |
| UGP1 | 13 | 1 | UDP-GLUCOSE PYROPHOSPHORYLASE 1 |
| GPHN | 12 | 1 | GEPHYRIN |
| PRKAG1 | 12 | 1 | PROTEIN KINASE, AMP-ACTIVATED, GAMMA 1 NON-CATALYTIC SUBUNIT |
| CCT7 | 11 | 1 | CHAPERONIN CONTAINING TCP1, SUBUNIT 7 (ETA) |
| HSPA8 | 11 | 2 | HEAT SHOCK 70 kDa PROTEIN 8 |
| HSPA9 | 11 | 1 | HEAT SHOCK 70 kDa PROTEIN 9B (MORTALIN-2) |
| POLDIP2 | 11 | 1 | POLYMERASE (DNA-DIRECTED), DELTA INTERACTING PROTEIN 2 |
| SCN10A | 11 | 1 | SODIUM CHANNEL, VOLTAGE-GATED, TYPE X, ALPHA |
| GOPC | 10 | 1 | GOLGI ASSOCIATED PDZ AND COILED-COIL MOTIF CONTAINING |
| NUDT19 | 10 | 1 | NUDIX (NUCLEOSIDE DIPHOSPHATE LINKED MOIETY X)-TYPE MOTIF 19 |
| TUFM | 10 | 1 | TU TRANSLATION ELONGATION FACTOR, MITOCHONDRIAL |
| ADPGK | 9 | 1 | ADP-DEPENDENT GLUCOKINASE |
| CARS2 | 9 | 1 | HYPOTHETICAL PROTEIN FLJ12118 |
| EXOSC10 | 9 | 1 | EXOSOME COMPONENT 10 |
| HNRPH1 | 9 | 1 | HETEROGENEOUS NUCLEAR RIBONUCLEOPROTEIN H1 |
| PRKAB1 | 9 | 1 | PROTEIN KINASE, AMP-ACTIVATED, BETA 1 NON-CATALYTIC SUBUNIT |
| ACTN3 | 8 | 1 | ACTININ, ALPHA 3 |
| ALAD | 8 | 1 | AMINOLEVULINATE, DELTA-, DEHYDRATASE |
| ATXN2L | 8 | 1 | ATAXIN 2-LIKE |
| CCT4 | 8 | 1 | CHAPERONIN CONTAINING TCP1, SUBUNIT 4 (DELTA) |
| HTRA2 | 8 | 1 | HTRA SERINE PEPTIDASE 2 |
| UBR4 | 8 | 1 | ZINC FINGER, UBR1 TYPE 1 |
| CCDC50 | 7 | 1 | COILED-COIL DOMAIN CONTAINING 50 |
| CHD9 | 7 | 1 | HYPOTHETICAL PROTEIN BC022889 |
| FAM175B | 7 | 1 | UNKNOWN PROTEIN |
| KIF14 | 7 | 1 | KINESIN FAMILY MEMBER 14 |
| P15RS | 7 | 1 | REGULATION OF NUCLEAR pre-mRNA DOMAIN CONTAINING 1A |
| RILPL1 | 7 | 1 | RAB INTERACTING LYSOSOMAL PROTEIN-LIKE 1 |
| SHROOM3 | 7 | 3 | SHROOM3 F-ACTIN BINDING PROTEIN |
| TF | 7 | 1 | TRANSFERRIN |
| CNDP2 | 6 | 1 | CNDP DIPEPTIDASE 2 (METALLOPEPTIDASE M20 FAMILY) |
| FLJ12529 | 6 | 1 | PRE-MRNA CLEAVAGE FACTOR I, 59 kDa SUBUNIT |
| PBEF1 | 6 | 1 | PRE-B-CELL COLONY ENHANCING FACTOR 1 |
| PPP1R9A | 6 | 1 | PROTEIN PHOSPHATASE 1, REGULATORY (INHIBITOR) SUBUNIT 9A |
| RB1CC1 | 6 | 1 | RB1-INDUCIBLE COILED-COIL 1 |
| SERBP1 | 6 | 1 | SERPINE1 MRNA BINDING PROTEIN 1 |
| ACLY | 5 | 1 | ATP CITRATE LYASE |
| CTTN | 5 | 1 | CORTACTIN |
| CUL-5 | 5 | 1 | CULLIN 5 |
| FHL1 | 5 | 1 | FOUR AND A HALF LIM DOMAINS 1 |
| IDH3A | 5 | 1 | ISOCITRATE DEHYDROGENASE 3 (NAD+) ALPHA |
| SAP130 | 5 | 1 | SIN3A-ASSOCIATED PROTEIN, 130 kDa |

TABLE 1-continued

Proteins Binding to αIIb

| Gene Symbol | # Peptides | No. Expts | Description |
|---|---|---|---|
| WARS2 | 5 | 1 | TRYPTOPHANYL TRNA SYNTHETASE 2 |
| ADCY6 | 4 | 1 | ADENYLATE CYCLASE 6 |
| C5orf25 | 4 | 1 | FLJ44216 PROTEIN |
| CIT | 4 | 1 | CITRON (RHO-INTERACTING, SERINE/THREONINE KINASE 21) |
| EEF2K | 4 | 1 | EUKARYOTIC ELONGATION FACTOR-2 KINASE |
| FLJ22184 | 4 | 1 | HYPOTHETICAL PROTEIN FLJ22184 |
| FRMPD1 | 4 | 1 | FERM AND PDZ DOMAIN CONTAINING 1 |
| HMGCS1 | 4 | 1 | 3-HYDROXY-3-METHYLGLUTARYL-COENZYME A SYNTHASE 1 (SOLUBLE) |
| NAGK | 4 | 1 | N-ACETYLGLUCOSAMINE KINASE |
| PRDX3 | 4 | 1 | PEROXIREDOXIN 3 |
| SF1 | 4 | 1 | SPLICING FACTOR 1 |
| TIMM50 | 4 | 1 | TRANSLOCASE OF INNER MITOCHONDRIAL MEMBRANE 50 HOMOLOG |
| AER61 | 3 | 1 | GLUCOSYLTRANSFERASE AER61 |
| CSNK2A2 | 3 | 1 | CASEIN KINASE 2, ALPHA PRIME POLYPEPTIDE |
| DHX38 | 3 | 1 | DEAH (ASP-GLU-ALA-HIS) BOX POLYPEPTIDE 38 |
| DVL2 | 3 | 1 | DISHEVELLED, DSH HOMOLOG 2 (*DROSOPHILA*) |
| ELMO1 | 3 | 1 | ENGULFMENT AND CELL MOTILITY 1 |
| GAPDH | 3 | 1 | GLYCERALDEHYDE-3-PHOSPHATE DEHYDROGENASE |
| KIAA0895 | 3 | 1 | KIAA0895 PROTEIN |
| KRT19 | 3 | 1 | KERATIN 19 |
| LUC7L2 | 3 | 1 | CGI-59 PROTEIN |
| MPO | 3 | 1 | MYELOPEROXIDASE |
| PEG10 | 3 | 1 | PATERNALLY EXPRESSED 10 |
| RPLP0 | 3 | 1 | RIBOSOMAL PROTEIN, LARGE, P0 |
| SEC13 | 3 | 1 | SEC13-LIKE 1 (*S. CEREVISIAE*) |
| SEC23A | 3 | 1 | SEC23 HOMOLOG A (*S. CEREVISIAE*) |
| SEMG1 | 3 | 1 | SEMENOGELIN I |
| ZFN300 | 3 | 1 | ZINC FINGER PROTEIN 300 |
| A2M | 2 | 1 | ALPHA-2-MACROGLOBULIN |
| ABCA13 | 2 | 1 | ATP-BINDING CASSETTE, SUB-FAMILY A (ABC1), MEMBER 13 |
| ATP5A1 | 2 | 1 | ATP SYNTHASE, H+ TRANSPORTING, MITOCHONDRIAL F1 COMPLEX, ALPHA SUBUNIT 1, CARDIAC MUSCLE |
| CCNB2 | 2 | 1 | CYCLIN B2 |
| CORO1A | 2 | 1 | CORONIN, ACTIN BINDING PROTEIN, 1A |
| CYCG1 | 2 | 1 | CYCLIN G1 |
| GRIN2D | 2 | 1 | GLUTAMATE RECEPTOR, IONOTROPIC, N-METHYL D-ASPARTATE 2D |
| MAP3K7IP2 | 2 | 1 | MITOGEN-ACTIVATED PROTEIN KINASE KINASE KINASE 7 INTERACTING PROTEIN 2 |
| NARS2 | 2 | 1 | ASPARAGINYL-TRNA SYNTHETASE 2 |
| PDLIM7 | 2 | 1 | PDZ AND LIM DOMAIN 7 (ENIGMA) |
| PPP1CA | 2 | 1 | PROTEIN PHOSPHATASE 1, CATALYTIC SUBUNIT, ALPHA ISOFORM |
| PTCHD2 | 2 | 1 | PATCHED DOMAIN CONTAINING 2 |
| RANBP10 | 2 | 1 | RAN BINDING PROTEIN 10 |
| RAVER1 | 2 | 1 | RAVER1 |
| SOX6 | 2 | 1 | SRY (SEX DETERMINING REGION Y)-BOX 6 |
| STMN3 | 2 | 1 | STATHMIN-LIKE 3 |
| ZNF703 | 2 | 1 | ZINC FINGER PROTEIN 703 |
| CCNK | 1 | 1 | CYCLIN K |
| HOMER3 | 1 | 1 | HOMER HOMOLOG 3 (*DROSOPHILA*) |
| U2AF1 | 1 | 1 | U2(RNU2) SMALL NUCLEAR RNA AUXILIARY FACTOR 1 |

Gene Ontology analysis of the αIIb interactome. Gene ontology analysis using the DAVID Bioinformatics Resources (Huang, *Nat. Protoc.*, 4:44 (2009), Dennis, *Genome Biol.*, 4:P3 (2003)) categorized the 123 proteins retrieved from αIIb complexes as: organelle component (84), protein transport (42), apoptosis (41), nucleotide binding (37), cytoskeleton (28), protein folding (28), response to stress (25), kinases (25), actin metabolism (17), and ER associated (15). Similar analysis of the proteins retrieved from pro-αIIb complexes categorized them as: organelle component (79), nucleotide binding (38), protein transport (29), response to stress (26), cytoskeleton (25), ER associated (16), apoptosis (16), actin metabolism (14), and vesicle component (12). Both lists of proteins show enrichment for protein processing and trafficking proteins. (Table 1).

By combining αIIb interaction data with interaction data retrieved using the Cytoscape software (Yeung, *Curr. Protoc. Bioinformatics*, 8:813 (2008), Cline, *Nat. Protoc.*, 2:2366 (2007)) subgroups of mutually interacting proteins were identified. One such group included the chaperone proteins encoded by HSPA8, HSPA9, HSPA5 and DNAJC10 (Table 1). The protein encoded by HSPA8, designated heat shock 70 kDa protein 8, binds to nascent polypeptides to facilitate correct folding, and has also been identified as an ATPase in the disassembly of clathrin-coated vesicles during transport of membrane components through the cell. Of note, the yeast homologue of HSPA8, SSB1/2, was shown to interact directly with both the ribosome and the translating protein. In yeast, SSB1/2 is the core chaperone in a chaperone complex that serves as the primary folding apparatus for nascent proteins. The HSPA9 protein, designated mortalin, is a chaperone and is also an inhibitor of apoptosis. HSPA5, or BiP, has been shown to interact with αIIb. DNAJC10, an HSP40 type chaperone, has not previously been reported to interact with αIIb or β3. Therefore, this novel interaction between αIIb and DNAJC10 was investigated.

Figure 5:
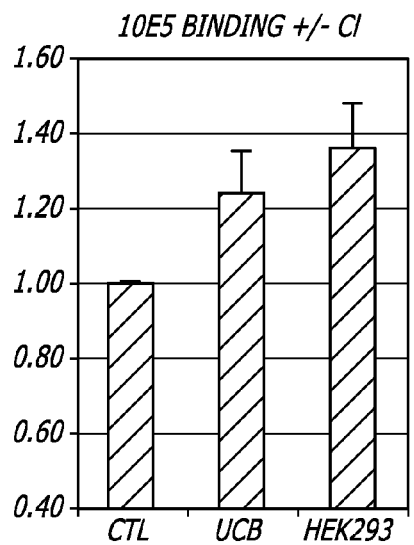
FIG. 5 demonstrates siRNA mediated knockdown of DNAJC10 increased surface expression of αIIbβ3 in UCB megakaryocytes and HEK293 cells compared to control siRNA transfection.

DNAJC10 in αIIbβ3 biogenesis. Immunoprecipitation of αIIb and β3 with mAbs CA3 and 7H2, respectively, followed by immunoblot with anti-DNAJC10 mAb revealed protein bands corresponding to the molecular mass of DNAJC10, indicating direct or indirect physical interaction of αIIb and β3 with DNAJC10 (FIG. 5). However, the band representing DNAJC10 precipitation with αIIb was very faint compared to that of β3. To explore the possibility that DNAJC10 interacted with αIIb prior to proteasomal degradation of αIIb, UCB-derived megakaryocytes were incubated with the proteasome inhibitor MG132 before immunoprecipitation with αIIb or β3 specific mAbs. An increase was seen in the amount of DNAJC10 immunoprecipitated with both αIIb and β3, suggesting that αIIb-DNAJC10 association occurs prior to the normal proteasomal degradation of excess or misfolded αIIb. The finding that proteasome inhibition increased αIIb-DNAJC10 interaction suggested that this interaction takes places at an early stage in αIIbβ3 biogenesis. To test this, αIIb was immunoprecipitated from megakaryocytes in the presence of MG132 using the mAbs: 10E5, which recognizes both the pro-αIIbβ3 and mature αIIbβ3 complexes, B1B5, which preferentially recognizes pro-αIIb, and M148, which preferentially recognizes mature αIIb. Equal amounts of protein were separated on an SDS gel and immunoblotted for DNAJC10. DNAJC10 was strongly immunoprecipitated by B1B5 and less so by M148, suggesting that DNAJC10 preferentially interacts with pro-αIIb. To determine whether the αIIb-DNAJC10 interaction impacted the end-point expression of αIIbβ3, siRNA mediated knockdown of DNAJC10 was performed on both human megakaryocytes derived from umbilical cord blood and on HEK293 cells expressing normal αIIb and β3 (FIG. 5). Knockdown of DNAJC10 increased αIIbβ3 surface expression on megakaryocytes by 25%+/−11% (n=4, p=0.02), and on HEK293 cells expressing αIIbβ3 by 35%+/−12% (n=4, p=0.01). Overexpression of DNAJC10 cDNA resulted in no change in the level of surface expression of αIIbβ3 on human megakaryocytes.

Example 6

Mutations in blades 4-7 of the αIIb β-propeller result in ER retention. Normal αIIb or αIIbG128S, a Glanzmann mutation, along with normal β3 were expressed into HEK293 cells and the localization of the subunits was analyzed with confocal microscopy. Transfected cells were labeled with an anti-αIIb antibody and an antibody to the ER component calnexin. Cells transfected with normal αIIbβ3 showed strong labeling of the cell surface, indicating "normal" αIIbβ3 surface expression. In addition, there is αIIb staining throughout the cell, some of which co-localizes with calnexin. In contrast, αIIb was not observed on the surface of cells transfected with the mutant αIIbβ3, but strongly co-localized with calnexin. Further studies showed lack of progression of the mutant αIIb to the Golgi.

Example 7

The Network of Chaperone and Transport Proteins that Interact with αIIb and β3 During Biogenesis The αIIb and β3 subunits are synthesized independently in the ER, where they form a heterodimer complex. Pro-αIIb subunits exist as monomers in the ER prior to heterodimers formation and are produced in excess of what is used for complex formation. Free pro-αIIb does not exit the ER, even when expressed as a "soluble" form without its transmembrane or cytoplasmic domains. Mature αIIb appears to exist only in complex with β3, and has not been identified as a monomer. Additionally, only mature αIIbβ3 has been detected on the platelet and megakaryocyte surface. Together these findings indicate that heterodimer formation is necessary for pro-αIIb cleavage into mature αIIb, which is necessary for egress to the cell surface. Thus, both of these processes represent critical control points in the regulation of αIIbβ3 surface expression, and both processes involve changes in the state of the αIIb subunit. Stepwise interactions of αIIb with limited subsets of chaperone and transport proteins guide αIIb and β3 through biogenesis, and the structural determinants of these interactions are on the αIIb subunit.

Affinity capture or crosslinking followed by mass spectrometry analysis, and is followed by confirmation of those interactions by co-immunoprecipitation with specific antibodies. To capture proteins that preferentially interact with pro-αIIb, an αIIb subunit harboring R858G and R859G mutations is used, which eliminates one of the furin cleavage sites, trapping αIIb in the pro-αIIb form. Next, a phenotypic screen of a siRNA library consisting of known ER and Golgi proteins is used to identify those functionally linked to αIIbβ3 surface expression. Putative interacting proteins are analyzed for specific interaction with αIIb and β3, and their role in αIIbβ3 biogenesis is determined.

Identify proteins that physically interact with αIIb in megakaryocytes during αIIbβ3 biogenesis. Affinity capture or photo-crosslinking is used followed by mass spectrometry to identify proteins that interact with αIIb in UCB-derived megakaryocytes. In order to capture αIIb interactions occurring during megakaryopoiesis and not in the mature proplatelet processes, day eight megakaryocytes are analyzed, which in this system express αIIbβ3 on the surface but have not begun proplatelet formation. Two different conformations of αIIb, representing precursor and mature αIIb subunits, are used to distinguish between proteins that differentially interact with the two conformations. The first method is a two-cell pulldown assay using histidine-tagged αIIb as bait. The His-tagged proteins are expressed in HEK293 cells with β3, extracted with nickel beads, and the beads are washed 4 times with buffer containing 500 mM Na (until no further protein can be detected in the wash by Coumassie stain). Fresh whole cell lysates from UCB-derived megakaryocytes are then incubated with the washed, nickel-bound αIIb. The beads are washed, the nickel-bound proteins are eluted with imidazole, and the entire eluate is subjected to SDS-PAGE followed by Coumassie stain. Experimental and control lanes are cut out and analyzed by mass spectrometry at the Rockefeller University Proteomics Core facility (New York, N.Y.). The second method utilizes photoreactive crosslinking amino acids to identify potential protein complexes involving αIIb and β3. UCB megakaryocytes are starved for methionine and leucine, and then "fed" photoreactive methionine and leucine, which should be incorporated into new proteins. 24 hours later the cells are exposed to UV light to cause crosslinking between the photoreactive amino acids. The cells are lysed, and the lysates are immunoprecipitated with anti-αIIb or anti-β3 mAbs to extract the complexes, which are analyzed by mass spectrometry.

Protein identification by mass spectrometry is considered "positive" if there are at least two peptides with a MASCOT score (Matrix Science) of at least 40, meaning that they have been reliably identified by the mass spectrometry. These specifications are of somewhat low stringency. Manual validation of the peptide sequences derived from the corresponding MS/MS spectra to increase the reliability of identified proteins is conducted.

To eliminate as many false positives as possible, control lanes are analyzed simultaneously in each experiment, and proteins in those lanes are removed from the data set. For controls in the His-tag/nickel bead binding assay, the His-tagged proteins are incubated with lysis buffer only (no megakaryocytes lysate). This identifies proteins from the HEK293 cells that remain bound after washing, as well as proteins with naturally occurring polyhistidine sequences (such as DEAH boxes) or nickel binding activity. For controls of the crosslinking extractions, cell lysates are reacted with species- and subtype-matched non-immune IgG.

Since proteins that bind strongly to αIIb in the HEK293 cells (e.g. β3) might not be removed even after multiple washes, false negatives can appear in the control lanes as well as the experimental lanes. The recommended UV source has been obtained and preliminary studies are performed to maximize crosslinking efficiency and minimize toxicity.

Proteins identified by mass spectrometry are evaluated using the DAVID web tool (NCBI) which can organize the putative interacting proteins by Gene Ontology (GO) annotation into functional categories, which helps to identify potentially interesting protein (e.g. transport and chaperone proteins) as well as proteins to exclude (e.g. mitochondrial proteins). The protein list is analyzed using the Cytoscape software (Yeung, Curr. Protoc. Bioinformatics, 8:813 (2008), Cline, Nat. Protoc., 2:2366 (2007)).

Given the complexity of the interpretations of positives and negatives, the proteins in the final list are evaluated individually. Mitochondrial proteins are removed from the list, and potential false-positives are the lowest priority for evaluation.

Example 8

ER and Golgi Proteins that Functionally Affect αIIbβ3 Surface Expression

UCB-derived megakaryocytes are used to screen a custom siRNA library obtained from ABI consisting of 150 ER and Golgi proteins, compiled by searching for GO categories involving those two organelles. There are 4 siRNA duplexes per protein. Some proteins deemed very unlikely to be directly involved in αIIbβ3 biogenesis are excluded. For example, proteins involved in O-linked glycosylation are excluded, since neither αIIb nor β3 are O-glycosylated. Screening criteria is percent change in αIIbβ3 surface expression, as judged by binding of the complex-dependent mAb 10E5. The experiments are performed in triplicate in 96 well plates. Non-targeting, PE-labeled siRNA marker duplex is co-transfected with each well to determine the transfection efficiency and mark the transfected cells. Cells are transfected on days 3 and 5 of culture and analyzed by flow cytometry on day 8-9. In preliminary experiments, the transfection efficiency has been 50%, and the variance of the mean fluorescent intensity (MFI) of 10E5 binding between replicate experiments has been 10%, so that a change of more than 10% from control is necessary to identify an effect from the siRNA. Changes of greater magnitude for several proteins have been documented thus far. Simultaneous controls are run in each plate: a) non-treatment to control for the effects of transfection and RNA exposure, transfection reagent only without siRNA to control for transfection reagent, transfection with non-targeting, unlabeled siRNA (Dharmacon Waltham, Mass.) to control for nonspecific effects of transfection, transfection with the labeled non-targeting siRNA to control for the effects of the fluorescent label, and a known positive siRNA (anti-cyclophilin, which stops cell growth, providing an easy phenotypic readout).

Changes in the binding of 10E5 may represent a real change in the surface expression of αIIbβ3. Thus, screening for siRNA effects on αIIbβ3 surface expression in megakaryocytes could identify novel proteins that are involved in the processing/trafficking events required for delivery of membrane proteins to proplatelets. To eliminate false positives, any putative hits are validated by further analyses, including: a) flow cytometry analysis of cell viability and of other surface proteins (such as GP1b) to determine specificity, b) QRTPCR to verify knockdown of the specific mRNA, using the CYBR green method with Qiagen primer sets (Quiagen), and correcting for the transfection efficiency, and c) co-immunoprecipitation of αIIb or β3 with the putative protein and immunoblot with specific mAbs.

Example 9

Validate the Physical Interactions and Determine the Functional Significance of the Putative Protein Interactions with αIIb and β3

The highest scoring and most interesting proteins identified above are analyzed to reveal their potential functions. The basic confirmatory assay for the putative interacting proteins is co-immunoprecipitation with αIIb and β3 from freshly prepared megakaryocyte lysate and immunoblot with protein-specific monoclonal or polyclonal antibodies. If specific antibodies are not obtained, metabolic labeling can be used to determine whether a protein of the appropriate Mr co-immunoprecipitates with αIIbβ3, then a mAb is generated by the mAb Core Facility at the New York Blood Center.

Both αIIb and β3 progress through several distinct conformational states during their biosynthesis, and these distinct states can be selectively immunoprecipitated by conformation-specific mAbs. Co-immunoprecipitation of the putative proteins with a panel of conformation-specific mAbs is used to determine which conformation(s) interact(s) with the putative proteins. From these data we determine at what point in the αIIbβ3 production cycle the interaction occurs.

RNAi-mediated knockdown and cDNA overexpression is used assess the gross functionality of the putative proteins. RNA knockdown is initially be performed with pooled siRNA duplexes purchased from Dharmacon, using the Dharmafect 1 reagent. Conditions optimized for UCB-derived megakaryocytes use 300 nM siRNA with duplicate transfections on days 3 and 5 of culture. HEK293 cells use 100 nM siRNA. For greater efficiency and greater knockdown an shRNA expressed from a lentiviral vector can be used. A Tet-on shRNA was constructed expressing lentiviral vectors using the pLVCT-tTR-KRAB and pLVTHM vectors obtained from AddGene (Cambridge, Mass.). The shRNAs are designed using the sequences of the siRNA duplexes from Dharmacon as templates. The shRNA oligos are purchased from Operon (Huntsville, Ala.) and ligated into the pLVTHM vector, and then the segment containing the Tet-response element, the H1 promoter and the shRNA is excised and ligated into the pLVCT-tTR-KRAB vector, which also expresses an EGFP for selection of infected cells. At least 3 shRNA vectors per protein are made to be studied to control for off-target effects. Studies to test the functionality of the shRNA are performed in HEK293 cells. The Tet-on system is used because some of the proteins analyzed may have functions in early megakaryopoiesis unrelated to αIIbβ3 biogenesis. The Tet-on system silences the shRNA until doxycycline is added after 7-8 days of UCB culture.

In order to overexpress cDNA of putative proteins the same pLVCT-tTR-KRAB backbone is modified by creating Gateway (Invitrogen) recombination sites flanking the cDNA insertion site. This allows for rapid insertion of cDNAs acquired from AddGene (Cambridge, Mass.), which are in the Gateway-compatible Sport6 vector, into the pLVCT-tTR-KRAB vector via the Gateway system, which uses recombination rather than ligation. To identify the infected cells, the Tet repressor protein cDNA (which is expressed through an internal ribosomal entry site from the cDNA promoter) is replaced with zGreen cDNA from the pIRES2-ZsGreen1 vector (Clontech, Mountain View, Calif.), which allows visual or FACS identification of infected cells. Control vector has GFP in place of the cDNA. Infectious particles are made by cotransfecting the pLVCT-tTR-KRAB vector, the packaging vector psPAX2, and the VSVG envelope vector into HEK293T cells, and collecting the medium from 24-72 h post-transfection. Viral titer is determined by infecting HEK293 cells with serial dilutions of the viral supernatant and determining the number of infectious particles per ml of medium. Megakaryocytes are infected with titers of 5-10 infectious particles per cell. The actual number is determined by optimizing infection efficiency in preliminary experiments. Cells are analyzed for surface expression of $\alpha IIb\beta 3$ by flow cytometry. Co-immunoprecipitation with $\alpha IIb$ and $\beta 3$ is used to further assess the putative interaction.

Co-immunoprecipitation of a putative protein with $\alpha IIb$ or $\beta 3$ from UCB-derived megakaryocyte lysate is essential and compelling evidence of their intracellular interaction. Since the protein interactions are likely to be transient and of low affinity, a mild detergent (Brij94) is used for lysis. Disulfide bonds are protected during lysis by addition of NEM to the lysis buffer. Chaperone proteins tend to adhere to sepharose beads, causing false positive bands, therefore, all experiments have simultaneous control co-immunoprecipitation with species and subtype-matched non-immune antibody.

In one study, DNAJC10 is identified as putatively interacting with both pro-$\alpha IIb$ and the total pool of $\alpha IIb$. DNAJC10 co-immunoprecipitated with $\alpha IIb\beta 3$, indicating that there is a true interaction. In experiments using the panel of conformation-specific mAbs, the mAb B1B5, which preferentially recognizes pro-$\alpha IIb$, is found to co-immunoprecipitate DNAJC10 with both pro-$\alpha IIb$ and $\beta 3$, while M148, which preferentially recognizes mature $\alpha IIb\beta 3$, did not recover DNAJC10. Interestingly, DNAJC10 co-immunoprecipitates with pro-$\alpha IIbR858G/R859G$ expressed alone in HEK293 cells, but does not co-immunoprecipitate with $\beta 3$ expressed alone. Together these findings indicate that DNAJC10 preferentially interacts with pro-$\alpha IIb$ and the pro-$\alpha IIb\beta 3$ complex, but releases the complex upon cleavage of pro-$\alpha IIb$ to mature $\alpha IIb$. These results place DNAJC10-$\alpha IIb\beta 3$ interaction from the point of complex formation up to the point of cleavage to mature $\alpha IIb\beta 3$. Spatially and functionally, this places the interactions at a crucial decision point in $\alpha IIb\beta 3$ biogenesis, from the point of heterodimer formation and ER egress up to cleavage to mature $\alpha IIb\beta 3$ in the trans Golgi.

Example 10

Mechanisms by which Three Highly Conserved Structural Motifs of $\alpha IIb$ Regulate its Post-Translational Processing and Trafficking Three highly conserved structural motifs on $\alpha IIb$ are regions known to be important in $\alpha IIb\beta 3$ biogenesis, and thus represent potential sites of interaction with chaperone and trafficking proteins. The first motif is a highly conserved surface on blades 5 and 6 of the $\alpha IIb$ $\beta$-propeller, a region whose mutation in Glanzmann thrombasthenia results in ER retention. The second motif is the positional pattern of N-glycosylation of the $\alpha IIb$ $\beta$-propeller, which has been previously reported to be the sites by which $\alpha IIb$ engages the calnexin cycle of ER protein quality control in early $\alpha IIb$ biogenesis (Mitchell et al., *Blood*, (2005)). The third motif is the loop containing the consensus sequences for furin cleavage, which transforms pro-$\alpha IIb$ to mature $\alpha IIb$. Without wishing to be bound by any particular theory, it is believed that chaperones interact with $\alpha IIb$ through these motifs to prevent further advancement of $\alpha IIb\beta 3$ through biogenesis, and that a structural event related to $\alpha IIb$ maturation terminates the interaction, allowing $\alpha IIb\beta 3$ to progress to the next step. Therefore protein interactions with these motifs mediate post-translational control of $\alpha IIb\beta 3$ biogenesis Identify proteins binding to a putative chaperone binding site on the $\alpha IIb$ $\beta$-propeller. Protein folding in eukaryotes is thought to proceed domain by domain. However, there is evidence that the most N-terminal domain of $\alpha IIb$, its $\beta$-propeller, does not completely fold until it forms a complex with $\beta 3$. The small $\beta$-sheet designated as the "cap" is recognized by the mAb 10E5 only upon $\alpha IIb\beta 3$ complex formation, even though it is not involved in the $\alpha$-$\beta$ interface. Interestingly, 10E5 binding locks the heterodimer together against high temperature/low pH dissociation, a fact that was exploited to produce the $\alpha IIb\beta 3$ crystal structure. The cap domain is in the first three "blades" of the $\alpha IIb$ $\beta$-propeller, and, importantly, only the first three blades are required to form a functional $\alpha$-$\beta$ heterodimer that binds RGD ligand. The remaining four blades of the propeller contain the four calcium-binding domains. The many mutations reported in this region, both in patients and experimentally, all share the two characteristics of allowing complex formation while preventing ER egress. Thus it appears that the function of the first three propeller blades is to capture $\beta 3$, and the function of the last four blades is to mediate ER retention. Following the baseline assumption that intracellular retention of $\alpha IIb$ is mediated by chaperone interactions that are terminated by maturation, and without wishing to be bound to any particular theory, it is thought that that blades 4-7 of the $\alpha IIb$ $\beta$-propeller have a chaperone interaction site when partially folded that is lost or becomes cryptic upon native folding of the $\beta$-propeller. It is further thought that this site is a highly conserved surface that stretches across propeller blades 5-6 but on the inside of the propeller, where it is hidden in the completely folded propeller $\beta$-propellers fold and close via a "zipper" mechanism in which the first synthesized strand is actually the last strand (strand 4) in the last blade of the propeller. Once the entire propeller is synthesized, strands 1-3 of blade seven join with the previously synthesized strand 4, zipping the propeller closed. It is thought that a putative chaperone protein binds to the exposed "inside" of the propeller, preventing egress from the ER, and is displaced when the propeller zips closed, releasing $\alpha IIb$ for egress. Mutations in this region, particularly in the calcium-binding domains, which both seed the folding of and rigidify $\beta$-sheets, might prevent the encryption of this motif and release from the putative chaperone. Accordingly, in this study, proteins interacting with this region of $\alpha IIb$ are identified by using a construct consisting of blades 4-7 of the $\beta$-propeller (Glu451 to Gly233) as bait for affinity capture, followed by mass spectrometry.

Example 11

Determine Whether the N-Glycans of the $\alpha IIb$ $\beta$-Propeller Regulate Expression Level It has been previously reported that the pattern of N-linked glycosylation on the $\alpha IIb$ $\beta$-propeller is positionally conserved across alpha integrins and that glycosylation at the N15 position is not only necessary for ER quality control of αIIb early in biogenesis, but may also play a role in αIIbβ3 assuming its bent, inactive conformation. In order to dissect out the mechanism of αIIbβ3 complex formation, conformational changes that the αIIb and β3 subunits undergo before and during complex formation were mapped. While β3 appears to be synthesized in its open, unbent conformation, pro-αIIb appears to be synthesized in its closed, bent conformation. Subsequently, the β3 subunit assumes its closed, bent conformation by virtue of attaching to pro-αIIb. Without wishing to be bound by any particular theory, it is thought that calnexin binding to the pro-αIIb headpiece may play a role in forcing pro-αIIb to assume its bent conformation, since calnexin is an integral membrane protein located near the membrane surface, and removal of the N15 glycan interfered with complex formation. This is the first proposal of a mechanism for inducing the inactive, bent-over conformation of αIIbβ3.

Whether the overall configuration of N-linked glycans on the αIIb β-propeller plays a role in αIIbβ3 expression is determined. The β3 integrin partners, αIIb and αv, share about 40% homology overall and almost 80% homology in the β-propeller. However, αIIbβ3 is very highly expressed on platelets (~80,000 copies/platelet) while αvβ3 is minimally expressed (~100 copies/platelet). One obvious structural difference is that αIIb has its first N-linked glycan at N15, on the first upward loop of propeller blade 1, while αv has its first N-linked glycan at N45, on the second upward loop propeller blade 1. The N-linked glycan sites on αIIb and αv are manipulated to test the hypothesis that the position of the β-propeller N-linked glycans regulates αIIbβ3 and αvβ3 expression level.

Example 12

Determine Whether the αIIb Furin Cleavage Loop is a αIIb Retention Signal

It is well established that α-β heterodimer formation is a prerequisite to αIIbβ3 surface expression in megakaryocytes. However, heterodimer formation is not sufficient for expression, as indicated by multiple patient and experimental mutations which permit α-β complex formation but result in intracellular retention. The required conformational change is furin cleavage of pro-αIIb to mature αIIb. Furin is a member of the proprotein convertase subtilisin-like protease family, and furin, PACE4 and PC5 have been shown to cleave integrins. Uncleaved pro-αIIb is not expressed on the megakaryocyte surface in vivo, although when pro-αIIb with mutations in the furin cleavage site is overexpressed in mammalian cell lines, it is not cleaved by furin and some does reach the cell surface.

In previous studies of the conformational changes of αIIb during complex formation, mAb epitopes on the pro-αIIb furin cleavage loop were not accessible on solitary pro-αIIb. This is despite the fact that the loop is external, unstructured in the crystal structure, and that these epitopes are exposed on the mature integrin after extension and leg-leg separation during activation. This loop is near the transmembrane region of αIIb, and it is possible that it is hidden by the membrane or "under" the αIIb leg region. However, it could also be hidden by binding of a chaperone protein. Without wishing to be bound by any particular theory, it is thought that a chaperone protein retains pro-αIIb in the ER and/or Golgi by binding to the loop region, but then releases αIIb upon furin cleavage of that loop.

Determine whether a highly conserved charged surface on the αIIb β-propeller mediates αIIb retention in the ER. To determine if a portion of the αIIb β-propeller is recognized and held in the ER by a chaperone protein (or proteins) until the β-propeller is completely folded or is bound to β3, binding partners of this segment are determined.

Blades 4-7 are expressed from Glu451 to Gly233, as a truncated, histidine-tagged, V5-tagged cDNA construct, and used for an affinity capture assay. Proteins captured with this construct are separated by SDS-PAGE and identified by mass spectrometry at the Rockefeller University proteomics core. Co-immunoprecipitation of the blades 4-7 construct (using the V5 epitope) is used to validate any putative interacting proteins. In addition, co-immunoprecipitation is used to assess interactions of the construct with any of the interacting proteins (e.g. DNAJC10). The contributions of the conserved surface to the binding of putative interacting proteins is assessed by alanine substitution of the conserved R303 and R368 residues in the blade 4-7 construct, followed by expression and co-immunoprecipitation analysis.

Proteins identified by mass spectrometry are evaluated. proteins with adequate MASCOT scores (Matrix Science) will be evaluated by GO annotation using DAVID, and the network visualization software Cytoscape. As before, high false-positives can result, particularly because the construct exposes surfaces that are usually hidden in the fully folded β-propeller. Controls are employed to decrease the number of false positives. A final list of proteins is individually evaluated and validated. Those proteins which fall into the potential false positive category are viewed with suspicion, and chaperone proteins specific to the mitochondrion will be eliminated from the final analysis.

Example 13

Determine Whether the Positions or Presence of the Asparagine-Linked Glycans on the αIIb β-Propeller Regulate αIIb Expression and Complex Formation Several glycosylation mutant αIIb cDNA constructs are made. These are in the pcDNA3.1 vector with V5 and poly-His tags. N15Q mutant and N249Q construct (quikchange xl from Stratagene) are used. Next, both the N15 and N249 glycosylation motifs on αIIb are eliminated by N to Q mutations. These three constructs are expressed in HEK293 cells with normal β3. αIIbβ3 expression is analyzed by western blot, flow cytometry, and pulse-chase experiments. Co-immunoprecipitation studies assess the binding of calnexin and calreticulin as indicators of αIIb engagement of the calnexin cycle.

Whether the position of the N-linked glycans on the propeller regulates αIIbβ3 expression level is evaluated. Complementary cDNA constructs of αIIb and αv are developed that have the positions of their N-linked glycans swapped. That is, the αIIb has a glycan on blade 2, loop 1, while αv has a glycan on blade 1, loop 1. An αv cDNA is constructed that is missing its first glycosylation site (N45) altogether. These constructs are expressed in HEK293 cells with normal β3, and analyzed using western blot, flow cytometry, pulse-chase, and co-immunoprecipitation studies.

The role of the calnexin cycle is investigated by using siRNA mediated knockdown or cDNA overexpression of the proteins in the calnexin cycle, and analyzing the effects on αIIbβ3 biogenesis. These experiments are performed on both HEK293 cells and UCB derived megakaryocytes and provide information on whether the interactions of the calnexin cycle are essential for αIIbβ3 surface expression.

Removing the N249 glycosylation site does not greatly impact αIIbβ3 biogenesis, since it is typically the glycans within 50 amino acids from the N-terminus that are regulated by the calnexin cycle. However, the double N deletion has defective biogenesis. This indicates that the N15 is the primary interacting point with the calnexin cycle and that the N249 plays an accessory role.

Example 14

Determine Whether the Loop Containing the Furin Cleavage Sites on αIIb Mediates βIIb Retention in the ER or Golgi The pLVCT lentiviral vector is used to express fluorescently tagged cDNA constructs of αIIb in UCB-derived megakaryocytes. In the first construct the αIIb furin cleavage motif, RXRR at 856-859, is eliminated by an R858GR859G mutation. In the second construct, the furin cleavage loop is removed altogether. This is made by deletion of residues 842 to 862, and the insertion of a GG bridge, using the splicing by overlap extension method. The expression pattern of these constructs indicates whether the furin cleavage loop is a retention signal. The effects of the cDNA constructs of the kinetics of αIIbβ3 biosynthesis are analyzed by pulse-chase metabolic labeling followed by immunoprecipitation with ant-GFP mAbs. The intracellular trafficking of the mutant αIIb is analyzed by immunofluorescence using organelle-specific markers and colocalization with the EGFP labeled αIIb. Confocal microscopy is performed at the New York Blood Center Microscopy Core Facility. To determine whether the overall amount of furin is a factor in αIIbβ3 surface expression furin is either overexpressed using the same vector system, or inhibited by treating cells with inhibitors of furin (CMK and Poly-R, both 50 μM) and the kinetics of αIIbβ3 synthesis are studied.

An important control is to ensure the EGFP tagged αIIb constructs traffic to the correct locations and perform the same functions as the normal αIIb. Kiefer demonstrated that the C-terminally tagged αIIb-GFP construct was expressed on the surface of CHO cells as an αIIbβ3 heterodimer, and bound fibrinogen, indicating that the C-terminal GFP did not interfere with its general trafficking and function (*Biochem. J.*, 357:529 (2001)), therefore, the distribution of normal αIIb construct is compared with that of the endogenous αIIb using confocal microscopy.

To compare the fate of the αIIb cDNAs in the megakaryocytes, the relative intensity of fluorescence in the ER, Golgi, and surface of infected cells is compared. If mutating or removing the furin cleavage loop also removes a negative regulator, the Golgi fluorescence to decrease (no bottleneck anymore) and the surface expression to increase. It is interesting to note that while the aIIbR858G/R859G construct is not cleaved to mature αIIb, it is somewhat expressed as pro-αIIbβ3 on the cell surface. Without wishing to be bound by any particular theory, a possible explanation is that while furin cannot cleave the loop, the putative restraining chaperone may not be able to interact with it either. This is consistent with hypothesis that loop cleavage is required for release from a putative chaperone that also binds to the loop region.

Example 14

Develop and Test a Kinetic Model of Post-Translational Regulation of αIIbβ3 Surface Expression in Order to Identify the Rate Limiting Steps The rate limiting steps in post-translational regulation of αIIbβ3 expression represent potential targets for therapeutic intervention. A more complete model of αIIbβ3 processing and trafficking through the megakaryocyte would provide this information. Existing models of αIIbβ3 biogenesis are generally at the organelle level; a protein-level model is needed in order to consider pharmacological manipulation. The protein interaction data derived above in combination with microscopic analysis of αIIbβ3 trafficking in living megakaryocytes is used to develop a model of αIIbβ3 biogenesis at the protein interaction level. These experiments link the putative chaperone proteins with their cellular topography, kinetics of interaction with αIIbβ3, and function. Validation of a model at the protein interaction level and determination of the kinetics of the individual sub-steps in αIIbβ3 biogenesis leads to determination of the rate limiting steps in post translational regulation of αIIbβ3 expression.

There are two points in the current model of αIIbβ3 biogenesis that stand out as rate-limiting for surface expression. The first process is formation of the α-β heterodimer. The second process is cleavage of pro-αIIb to mature αIIb by furin. This study determines the exact cellular locations and kinetics of these processes in megakaryocytes using fixed and live-cell confocal microscopy. Although these two processes are typically grouped together as an indicator of maturity, furin cleavage must happen later and at some distance (compartmentally) from complex formation, since the complex presumably forms in the ER and the furin enzymes are located in the trans Golgi.

Using lentiviral expression of either shRNA against, or cDNA of, the putative proteins, it is determined whether their decrease or increase perturbs the dynamics of the ER and Golgi processing of pro-αIIbβ3. From this information the model of αIIbβ3 biogenesis to the protein interaction level is refined and it is possible to pinpoint the rate-limiting interactions regulating αIIbβ3 expression. The model is then applied to determine whether perturbing these interactions can significantly modulate expression of αIIbβ3 in proplatelets formed from UCB-derived megakaryocytes.

Metabolic pulse-chase experiments reveal the rates of appearance or disappearance of specific conformations and complexes of αIIb and β3 during biogenesis. By measuring these rates with and without knockdown or overexpression of putative interacting proteins, the roles of those proteins in αIIbβ3 biogenesis are deduced. Thus, pulse-chase experiments are performed on shRNA and cDNA treated cells to measure the rates of initial protein folding, degradation, complex formation and maturation of αIIbβ3.

For imaging procedures, UCB are cultured, and on day 4 replated onto washed, poly-lysine coated coverslips in the bottoms of 24-well culture plates. The cells are cultured until day 8, and then fixed and permeabilized in methanol/acetone. After blocking in BSA, the cells are reacted with anti-αIIb, anti-β3, or anti-αIIbβ3 mAbs, along with organelle-specific marker antibodies. The cells are washed and reacted with appropriate fluorescently labeled secondary antibodies, then mounted with Pro-Long or other anti-fade mounting medium and imaged. Preliminary experiments are conducted to optimize the fixing, permeabilization, and antibody concentrations. Simultaneous control experiments include staining with secondary mAb only.

This system is manipulated in two basic ways. In one set of experiments, the cells are transduced with lentiviral constructs containing putative chaperone cDNA, or shRNA. In the second set of experiments, the cells are transduced with lentiviral vectors containing EGFP labeled αIIb cDNA.

It is determined whether the putative interacting protein has a role in maintaining the steady state compartmentalization of αIIb and β3. For example, if a protein interacts with pro-αIIb and targets it for degradation, then decrease of this protein might result in excessive buildup of pro-αIIb in the ER.

In experiments with EGFP-tagged αIIb, the trafficking of αIIb through the megakaryocyte is visualized. These experiments require comparative preliminary studies to determine whether the construct colocalizes exactly as the normal αIIb does. One advantage of this trafficking study is that the C-terminal EGFP is located outside the ER, and so does not interfere with intraluminal interactions, although it can obviously interfere with cytoplasmic interactions.

The first experiments are the colocalization of αIIb and β3 with the putative interacting proteins. Colocalization is repeated after overexpression or knockdown of the putative interacting proteins.

The use of EGFP tagged αIIb allows the use of photobleaching in live megakaryocytes. Since EGFP is sensitive to light, a strong laser exposure permanently inactivates it. This phenomenon is manipulated to observe protein dynamics in living cells.

Whether αIIb in the ER and Golgi is fixed in an unknown protein complex or is freely mobile is determined by photobleaching a small area of the ER or Golgi and then observing the fluorescence recovery after photobleaching (FRAP) of to that area. Since αIIb is a membrane protein, its maximal recovery speed is determined by the diffusion rate in the ER or Golgi membrane. If the fluorescence recovery is much slower, that finding would be consistent with αIIb interacting with a large protein complex. These experiments are performed in the presence of cyclohexamide to halt production of new proteins, which represents influx to the ER and Golgi rather than diffusion within these organelles.

Whether manipulations of the identified chaperone proteins affects αIIb localization in megakaryocytes that are extending proplatelets is determined. UCB derived cells that have been transduced with cDNA or shRNA constructs, or with αIIb constructs are cultured until day 10, then replated onto poly-L-lysine coated coverslips in a 24 well plate. Cells with proplatelet processes and evidence of transduction (fluorescence) are evaluated as in fixation and colocalization studies.

Metabolic pulse chase experiments are used to determine kinetic parameters. By combining the panel of conformation dependent mAbs with expression of cDNA or shRNA of putative interacting proteins, one can determine the developmental stages at which the target proteins impact αIIbβ3 biogenesis. For example, since DNAJC10 appears to preferentially bind pro-αIIbβ3, overexpression of its cDNA might result in a larger pool of pro-αIIbβ3 and a slower degradation rate if the protein has a retaining function. Conversely, DNAJC10 overexpression might result in a smaller pool of pro-αIIbβ3 and a faster rate of degradation if it has a degradation targeting function.

By studying GEFP tagged αIIb in both fixed and lining megakaryocytes, its pathway of production is defined at a very detailed level. This method overcomes the compartmental sequestering or limitations of antibody binding encountered with immunofluorescence. This method also allows the observation of trafficking of mutant αIIb constructs, such as the furin cleavage loop mutants. While the expression level of the construct is most likely very low as compared to the native αIIb, this is an advantage. First, there is ample β3 to interact with the mutant αIIb, and second, the amount of αIIb from the construct is unlikely to saturate any chaperone system.

As an example, experiments with DNAJC10 begin with colocalization studies. DNAJC10 and αIIb colocalize in the ER. After DNAJC10 overexpression, there is an increase in colocalization relative to expression in other compartments, suggesting that the αIIb is increasingly bound by DNAJC10. Alternately, there may be less colocalization, suggesting that the increased DNAJC10 is increasing the transit rate of αIIb through the ER. In this way inferences are made about the kinetic functions of the interacting proteins.

The diffusion rate, D, and the mobile fraction, M, are determined. The diffusion rates for freely moving proteins in various membranes, including the ER, have been published, and provide a baseline for comparison of measured D. If measured D is lower than the reported D for ER membranes, then the αIIb subunits may be interacting with large or fixed molecules (or formed an aggregate). If the D is higher, then the αIIb subunits may be undergoing directed transport. The M of the αIIb subunits is a measure of how much of the subunit is freely mobile. An increase or decrease in M would indicate that less or more of the αIIb is bound to immobile structures. When coupled with transduction of cDNA or shRNA of putative αIIb-interacting proteins, these simple measurements provide a great deal of information about the potential functions of these proteins.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

What is claimed is:

1. A method of preventing or treating a condition associated with platelet aggregation comprising administering a therapeutically effective amount of a composition that modifies an interaction of DNAJC10 with αIIbβ3 in a megakaryocyte, wherein the composition comprises a nucleic acid that decreases expression of DNAJC10 in the megakaryocyte.

2. The method of claim 1, wherein the condition is a thrombosis.

3. The method of claim 1, wherein the condition is selected from the group consisting of coronary artery thrombosis, atherosclerotic lesions, restenosis, arterial thrombosis, and a combination thereof.

4. The method of claim 1, wherein the composition is administered at a time selected from the group consisting of prior to the onset of the condition, at the onset of the condition, after the onset of the condition, and a combination thereof.

5. The method of claim 4, wherein the composition is administered during or after a medical procedure during which thrombosis may result.

6. The method of claim 5, wherein the medical procedure is selected from the group consisting of an angiogram, angioplasty, catheterization, placement of filter for deep vein thrombosis, placement of intra-arterial stent placement, and a combination thereof.

7. The method of claim 1, wherein the composition is administered via a route selected from the group consisting of parenteral, subcutaneous, intravenous, intramuscular, intraperitoneal, transdermal, oral, buccal route, and a combination thereof.

* * * * *